United States Patent
Albert et al.

(10) Patent No.: US 9,346,892 B2
(45) Date of Patent: *May 24, 2016

(54) METHODS FOR SYNTHESIS OF AN OLIGOPEPTIDE MICROARRAY

(75) Inventors: Tom Albert, Verona, WI (US); Todd Richmond, Mercer Island, WA (US); Matthew Rodesch, Stoughton, WI (US); Klaus-Peter Stengele, Pleiskirchen (DE); Jochen Buehler, Waldkraiburg (DE); Markus Ott, Wadern (DE)

(73) Assignee: ROCHE NIMBLE GEN, INC., Madison, WI (US)

( * ) Notice: Subject to any disclaimer, the term of this patent is extended or adjusted under 35 U.S.C. 154(b) by 1108 days.

This patent is subject to a terminal disclaimer.

(21) Appl. No.: 13/419,029

(22) Filed: Mar. 13, 2012

(65) Prior Publication Data

US 2012/0238477 A1    Sep. 20, 2012

Related U.S. Application Data

(60) Provisional application No. 61/454,156, filed on Mar. 18, 2011.

(51) Int. Cl.
   *C07K 5/00* (2006.01)
   *C07K 17/06* (2006.01)
   *B01J 19/00* (2006.01)
   (Continued)

(52) U.S. Cl.
   CPC .............. *C07K 17/06* (2013.01); *B01J 19/0046* (2013.01); *B82Y 30/00* (2013.01); *C40B 50/18* (2013.01); *B01J 2219/0061* (2013.01); *B01J 2219/00432* (2013.01); *B01J 2219/00439* (2013.01); *B01J 2219/00596* (2013.01); *B01J 2219/00626* (2013.01); *B01J 2219/00637* (2013.01); *B01J 2219/00659* (2013.01); *B01J 2219/00675* (2013.01); *B01J 2219/00711* (2013.01); *B01J 2219/00725* (2013.01)

(58) Field of Classification Search
   CPC ...... C07K 17/06; B01J 19/0046; B82Y 30/00
   USPC .......................................................... 530/300
   See application file for complete search history.

(56) References Cited

U.S. PATENT DOCUMENTS

| | | | |
|---|---|---|---|
| 8,658,572 B2 * | 2/2014 | Albert | G01N 33/6845 506/18 |
| 2005/0048566 A1 * | 3/2005 | Delisi | C07K 16/00 435/7.1 |

(Continued)

FOREIGN PATENT DOCUMENTS

| | | |
|---|---|---|
| WO | 04001033 A2 | 12/2003 |
| WO | 2008151146 A2 | 12/2008 |

OTHER PUBLICATIONS

Bhushan, K.R. "Light-directed maskless synthesis of peptide arrays using photolabile amiino acid monomers" Bol. Biomol.Chem., Apr. 2006: 1857-1859.*

(Continued)

*Primary Examiner* — Betty Forman
(74) *Attorney, Agent, or Firm* — Olga Kay

(57) ABSTRACT

An oligopeptide microarray and methods for the synthesis thereof are presented. Further presented is a microarray on a solid support comprising at least about 10,000 oligopeptide features per $cm^2$ and preferably at least about 50,000 oligopeptide features per $cm^2$.

36 Claims, 7 Drawing Sheets

| Amino acid | Half-live [min] | Wavelength | Exposure time |
|---|---|---|---|
| BzNPPOC-Tyr(t-Bu)-OH: | 2.7 | 365 nm | 2, 4, 6, 8, 10 min |
| BzNPPOC-Cys(Trt)-OH | 1.8 | 365 nm | |
| BzNPPOC-Cit-OH | 2.4 | 365 nm | |

(51) Int. Cl.
*C40B 50/18* (2006.01)
*B82Y 30/00* (2011.01)

(56) References Cited

U.S. PATENT DOCUMENTS

2005/0101763 A1* 5/2005 DeLisi .................. C07K 1/063 530/333
2008/0188380 A1* 8/2008 Chi ..................... B01J 19/0046 506/15
2010/0137600 A1 6/2010 Gao et al.

OTHER PUBLICATIONS

PubChem, NIH, US National Library of Medicine webpage "6-aminohexanoic acid" no date.*

Foder, S.P.A, et al., "Light-Directed, Spatially Addressable Parallel Chemical Synthesis," Science 251:767-773 (1991).

Foder, S.P.A, et al., "Multiplexed biochemical assays with biological chips," Nature 364: 555-556 (1993).

Hasan, Ahmad, et al., "Photolabile Protecting Groups for Nucleosides: Synthesis and Photodeprotection Rates," Tetrahedron 53: 4247-4264.

Patchornik, A. et al., "Photosensitive Protecting Groups," J Am Chem Society 21:6333-6335 (1970).

Pease, Ann C. et al., "Light-generated oligonucleotide arrays for rapid DNA sequence analysis," Proc. Natl. Acad. Sci. USA 91:5022-5026 (1994).

Singh-Gasson, Sangeet et al., "Maskless fabrication of light-directed oligonucleotide microarrays using a digital micromirror array," Nature Biotech 17:974-978 (1999).

Gao, X. et al., "High density peptide microarrays. In situ synthesis and applications," Molecular Diversity, vol. 8, No. 3, pp. 177-187 (2004).

Gu, Zhen and Tang, Yi, "Enzyme-assisted photolithography for spatial functionalization of hydrogels," Lab on a Chip10:1946-1951 (2010).

* cited by examiner

FIG. 1a  NPPOC-L-Phenylalanine

FIG. 1b  NPPOC-L-Leucine

FIG. 1c  NPPOC-L-Valine

FIG. 2a    NPPOC-L-Glycine

FIG. 2b    NPPOC-L-Glutamic Acid

FIG. 2c    NPPOC-(1-Trityl)-L-Histidine

FIG. 3a Benzoyl-NPPOC-L-Phenylalanine

Mol. Wt.: 165,19     Mol. Wt.: 345,75     Mol. Wt.: 105,99     Mol. Wt.: 476,48

FIG. 3b BzNPPOC-L-Methionine

Mol. Wt.: 149,21     Mol. Wt.: 347,75     Mol. Wt.: 105,99     Mol. Wt. 460,50

FIG. 3c Benzoyl-NPPOC-(t-Bu)-L-Tyrosine

Step 1:

Mol. Wt.: 459,53                                      Mol. Wt.: 237,29

Step 2:

Mol. Wt.: 237,29     Mol. Wt.: 105,99                    Mol. Wt.: 548,58

| Amino acid | Half-live [min] | Wave-length | Exposure time |
|---|---|---|---|
| NPPOC-Tyr(t-Bu)-OH | 9.6 | 365 nm | 2, 4, 6, 8, 10 min |
| NPPOC-Gly-OH | 2.6 | 365 nm | |
| NPPOC-Trp(Boc)-OH | 3.2 | 365 nm | |
| NPPOC-L-Phe-OH | 2.9 | 365 nm | |
| NPPOC-Arg(Pbf)-OH | 2.9 | 365 nm | |
| NPPOC-Cys(Trt)-OH | 3.3 | 365 nm | |
| NPPOC-Cit-OH | 2.3 | 365 nm | |

| Amino acid | Half-live [min] | Wave-length | Exposure time |
|---|---|---|---|
| BzNPPOC-Tyr(t-Bu)-OH: | 2.7 | 365 nm | 2, 4, 6, 8, 10 min |
| BzNPPOC-Cys(Trt)-OH | 1.8 | 365 nm | |
| BzNPPOC-Cit-OH | 2.4 | 365 nm | |

| Antibody | Epitope(s) |
| --- | --- |
| HPA007244 | QAVASIAGGIRNGYD (SEQ ID NO:1); ITSENVAERFGIS (SEQ ID NO:2) |
| HPA006198 | GCTCVQTAIEGNSLG (SEQ ID NO:3); QMPIIIAGNDQQ (SEQ ID NO:4) |
| HPA005552 | SRPTPSDMAIV (SEQ ID NO:5) |
| HPA001399 | SLLPGHVQAYQEAVK (SEQ ID NO:6); HTLEDQALYN (SEQ ID NO:7) |
| HPA000525 | NDLIERIQVDAY (SEQ ID NO:8) |
| HPA008333 | SVLQNQGREMMLVTSGAV (SEQ ID NO:9) |
| HPA005554 | LDAAVTFGPS (SEQ ID NO:10) |
| HPA010793 | WGGEDDDIAT (SEQ ID NO:11) |
| HPA001328 | FRGDGGSTTGLSATPPA (SEQ ID NO:12) |
| HPA001138 | KHMTRSQAEQLLK (SEQ ID NO:13) |
| HPA005992 | RRERRFGRDMETIGFA (SEQ ID NO:14) |
| HPA002384 | FWEGDFHRDMEALNVLP (SEQ ID NO:15) |
| HPA001223 | ERDGTLKPGDTI (SEQ ID NO:16); ILQQCDGKLDMLV (SEQ ID NO:17) |
| HPA001254 | QGQAIDDLMPAQK (SEQ ID NO:18) |
| HPA008835 | GKNKQSLDAVE (SEQ ID NO:19) |
| HPA001566 | SVGMIAGGTGIT (SEQ ID NO:20); AIMKDPDDHTV (SEQ ID NO:21); MIQYACLPNLDH (SEQ ID NO:22) |
| HPA000793 | WTSFLSGVNI (SEQ ID NO:23) |
| HPA006461 | GLKMVVPGLDGAQI (SEQ ID NO:24) |
| HPA007641 | MQTQQMLLNKEEAV (SEQ ID NO:25) |
| HPA006148 | EDGGIIRRIGTRGE (SEQ ID NO:26) |
| HPA000237 | HIPQAKALLQDK (SEQ ID NO:27); DPLGKQGYQLRQGD (SEQ ID NO:28); IGGPRSYTIAVA (SEQ ID NO:29) |
| HPA004701 | HPCRQPDTPT (SEQ ID NO:30) |
| HPA001249 | ATQCISDGKLNEGHT (SEQ ID NO:31) |
| HPA003494 | WWKAQSLTTGQEG (SEQ ID NO:32); RQLLAPGNT (SEQ ID NO:33) |
| HPA006723 | CNPDDMARDLEQ (SEQ ID NO:34) |
| HPA001334 | SFVPWQPRFMIHMCPST (SEQ ID NO:35); KEVFSGIKNSNE (SEQ ID NO:36); RYSWDCSPLSMFRRH (SEQ ID NO:37) |
| HPA001231 | NTERTIYVRDPTS (SEQ ID NO:38) |
| HPA008247 | WPESASSPPV (SEQ ID NO:39) |
| HPA001240 | DGGLRHWLRQNLP (SEQ ID NO:40); EPRDGIEPGHI (SEQ ID NO:41) |
| HPA000704 | NSINTEEVIN (SEQ ID NO:42) |
| HPA008467 | LSTLGIVFQG (SEQ ID NO:43); PISSCDTGTMANCERT (SEQ ID NO:44); IKPDGVQRGLVGE (SEQ ID NO:45) |
| HPA001303 | QKLQDIQRAMELLSACQ (SEQ ID NO:46) |
| HPA007308 | TTGGSGSMYS (SEQ ID NO:47); LTYSIGHTPADARI (SEQ ID NO:48); LFDLNFQAGFLMKK (SEQ ID NO:49) |
| HPA000571 | LQERAVLGANDP (SEQ ID NO:50); TAIRPHGIFGPRDPQLVP (SEQ ID NO:51) |
| HPA001788 | SGSSQGRNSPAPAVT (SEQ ID NO:52); NAATKIPTPIVGVK (SEQ ID NO:53) |
| HPA006314 | ISDGPSVSALTNGFDTPEERYQ (SEQ ID NO:54); YDEKRSQANGAGA (SEQ ID NO:55) |
| HPA006277 | SLDSLPQAVREFLE (SEQ ID NO:56); QRDTVPIPKTGLSQLGRWMSEEDFEK (SEQ ID NO:57); FPGCMKGRTMYVIPFSM (SEQ ID NO:58) |
| HPA002645 | GSNYWRNRVMMVAK (SEQ ID NO:59) |
| HPA003230 | PTLKIFRDGEEAGAYDGPRTADGIVSHLKKQAGPASVPLRTEEEFKKFISDKDASIVGFFDDSFSEAHSFLKAASNLRNDYRFAHTN (SEQ ID NO:60) |
| HPA003982 | TLCKPAPLTGTLEV (SEQ ID NO:61); DSRPPFLSRPA (SEQ ID NO:62); LYSRSGSLSG (SEQ ID NO:63) |
| HPA006782 | PETRTVAVKQLGVNPSTTGTQ (SEQ ID NO:64); LVNGLHPLTLRWEET (SEQ ID NO:65); QPDTPPGTPLVQDE (SEQ ID NO:66) |
| HPA002947 | LEPMAAKAWDKESE (SEQ ID NO:67) |
| HPA003049 | KFDWTFEQTVETAIT (SEQ ID NO:68) |
| HPA006700 | QTEARDLVERCMRVL (SEQ ID NO:69) |
| HPA007981 | DPHQRLTAKQVLQHPWVTQKD (SEQ ID NO:70); QLKPIESSILQRRVRKLPSTTL (SEQ ID NO:71) |
| HPA002867 | SCMANINGGNTKACTR (SEQ ID NO:72); TNLNKVSKIYPLPH (SEQ ID NO:73); VPDLSNFYAQ (SEQ ID NO:74) |
| HPA001401 | PVQGIINFEQKESNGPVKVWGSIKGL (SEQ ID NO:75); EFGDNTAGCTSAGPHFN (SEQ ID NO:76) |
| HPA003323 | IGLDTTIMMRSIPL (SEQ ID NO:77); GFDQQMSSMV (SEQ ID NO:78); DSTTKEDTGT (SEQ ID NO:79) |
| HPA005993 | KQTIGNSCGT (SEQ ID NO:80); DGHLYELDGRMPFPVN (SEQ ID NO:81) |
| HPA004769 | TQSKEAFAIGL (SEQ ID NO:82); VARMIIEALD (SEQ ID NO:83); SMDSFYKVLTEQ (SEQ ID NO:84) |
| HPA000660 | SAKRHLAEQFAVGEIITD (SEQ ID NO:85); KVESDNGPLFTELK (SEQ ID NO:86); NGKSYRFMIMDRFGSDLQK (SEQ ID NO:87) |
| HPA006988 | SETFEKSRLYQLDKS (SEQ ID NO:88) |

*FIG. 6*

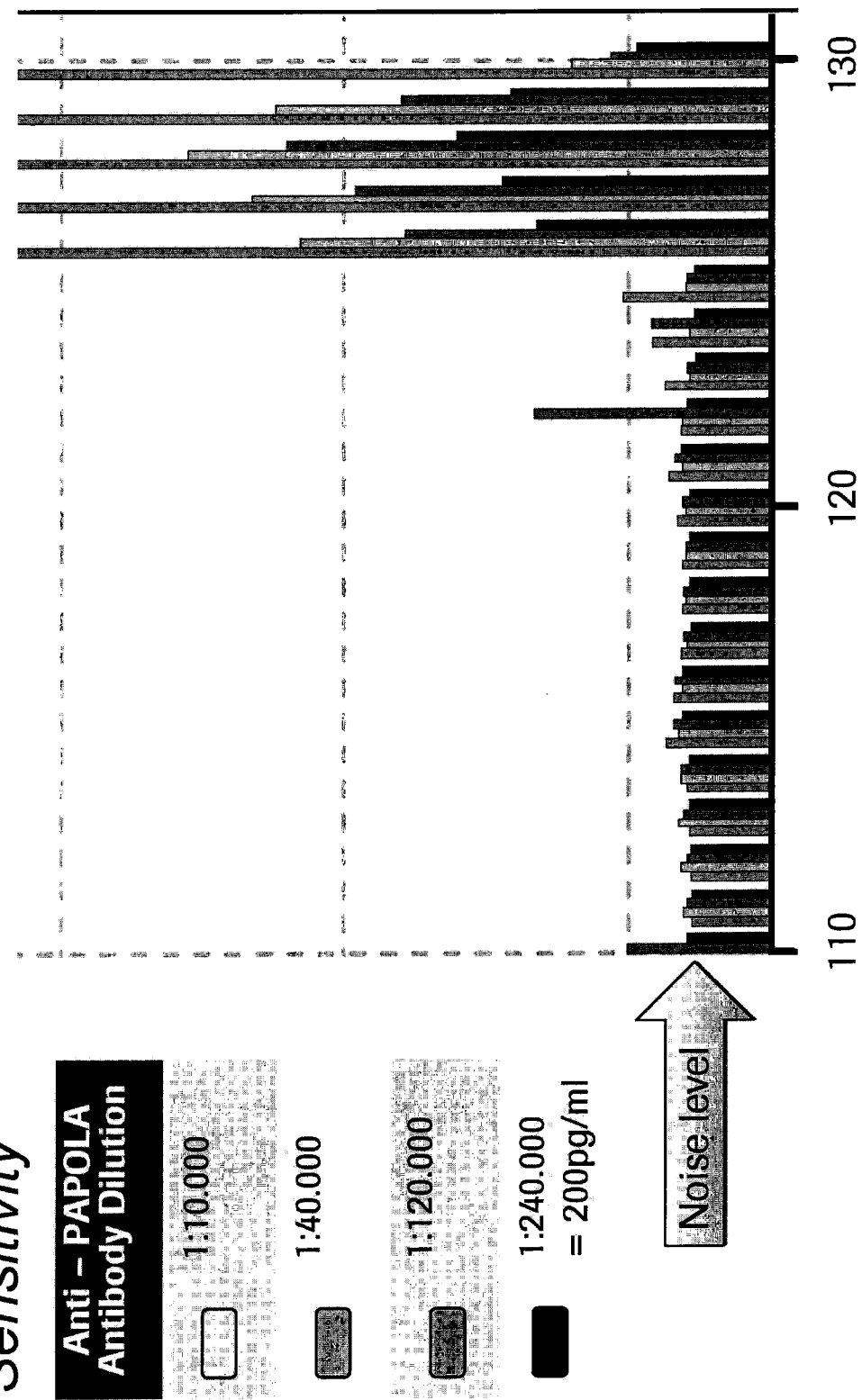

SEQUENCE LISTING

```
<160> NUMBER OF SEQ ID NOS: 88

<210> SEQ ID NO 1
<211> LENGTH: 15
<212> TYPE: PRT
<213> ORGANISM: Homo sapiens

<400> SEQUENCE: 1

Gln Ala Val Ala Ser Ile Ala Gly Gly Ile Arg Asn Gly Tyr Asp
1               5                   10                  15

<210> SEQ ID NO 2
<211> LENGTH: 13
<212> TYPE: PRT
<213> ORGANISM: Homo sapiens

<400> SEQUENCE: 2

Ile Thr Ser Glu Asn Val Ala Glu Arg Phe Gly Ile Ser
1               5                   10

<210> SEQ ID NO 3
<211> LENGTH: 15
<212> TYPE: PRT
<213> ORGANISM: Homo sapiens

<400> SEQUENCE: 3

Gly Cys Thr Cys Val Gln Thr Ala Ile Glu Gly Asn Ser Leu Gly
1               5                   10                  15

<210> SEQ ID NO 4
<211> LENGTH: 12
<212> TYPE: PRT
```

<213> ORGANISM: Homo sapiens

<400> SEQUENCE: 4

Gln Met Pro Ile Ile Ile Ala Gly Asn Asp Gln Gln
1               5                   10

<210> SEQ ID NO 5
<211> LENGTH: 11
<212> TYPE: PRT
<213> ORGANISM: Homo sapiens

<400> SEQUENCE: 5

Ser Arg Pro Thr Pro Ser Asp Met Ala Ile Val
1               5                   10

<210> SEQ ID NO 6
<211> LENGTH: 15
<212> TYPE: PRT
<213> ORGANISM: Homo sapiens

<400> SEQUENCE: 6

Ser Leu Leu Pro Gly His Val Gln Ala Tyr Gln Glu Ala Val Lys
1               5                   10                  15

<210> SEQ ID NO 7
<211> LENGTH: 10
<212> TYPE: PRT
<213> ORGANISM: Homo sapiens

<400> SEQUENCE: 7

His Thr Leu Glu Asp Gln Ala Leu Tyr Asn
1               5                   10

<210> SEQ ID NO 8
<211> LENGTH: 12
<212> TYPE: PRT
<213> ORGANISM: Homo sapiens

<400> SEQUENCE: 8

Asn Asp Leu Ile Glu Arg Ile Gln Val Asp Ala Tyr
1               5                   10

<210> SEQ ID NO 9
<211> LENGTH: 18
<212> TYPE: PRT
<213> ORGANISM: Homo sapiens

<400> SEQUENCE: 9

Ser Val Leu Gln Asn Gln Gly Arg Glu Met Met Leu Val Thr Ser Gly
1               5                   10                  15

Ala Val

<210> SEQ ID NO 10
<211> LENGTH: 10
<212> TYPE: PRT
<213> ORGANISM: Homo sapiens

<400> SEQUENCE: 10

Leu Asp Ala Ala Val Thr Phe Gly Pro Ser
1               5                   10

<210> SEQ ID NO 11
<211> LENGTH: 10
<212> TYPE: PRT

```
<213> ORGANISM: Homo sapiens

<400> SEQUENCE: 11

Trp Gly Gly Glu Asp Asp Asp Ile Ala Thr
1               5                   10

<210> SEQ ID NO 12
<211> LENGTH: 17
<212> TYPE: PRT
<213> ORGANISM: Homo sapiens

<400> SEQUENCE: 12

Phe Arg Gly Asp Gly Gly Ser Thr Thr Gly Leu Ser Ala Thr Pro Pro
1               5                   10                  15

Ala

<210> SEQ ID NO 13
<211> LENGTH: 13
<212> TYPE: PRT
<213> ORGANISM: Homo sapiens

<400> SEQUENCE: 13

Lys His Met Thr Arg Ser Gln Ala Glu Gln Leu Leu Lys
1               5                   10

<210> SEQ ID NO 14
<211> LENGTH: 16
<212> TYPE: PRT
<213> ORGANISM: Homo sapiens

<400> SEQUENCE: 14

Arg Arg Glu Arg Arg Phe Gly Arg Asp Met Glu Thr Ile Gly Phe Ala
1               5                   10                  15

<210> SEQ ID NO 15
<211> LENGTH: 17
<212> TYPE: PRT
<213> ORGANISM: Homo sapiens

<400> SEQUENCE: 15

Phe Trp Glu Gly Asp Phe His Arg Asp Met Glu Ala Leu Asn Val Leu
1               5                   10                  15

Pro

<210> SEQ ID NO 16
<211> LENGTH: 12
<212> TYPE: PRT
<213> ORGANISM: Homo sapiens

<400> SEQUENCE: 16

Glu Arg Asp Gly Thr Leu Lys Pro Gly Asp Thr Ile
1               5                   10

<210> SEQ ID NO 17
<211> LENGTH: 13
<212> TYPE: PRT
<213> ORGANISM: Homo sapiens

<400> SEQUENCE: 17

Ile Leu Gln Gln Cys Asp Gly Lys Leu Asp Met Leu Val
1               5                   10

<210> SEQ ID NO 18
```

```
<211> LENGTH: 13
<212> TYPE: PRT
<213> ORGANISM: Homo sapiens

<400> SEQUENCE: 18

Gln Gly Gln Ala Ile Asp Asp Leu Met Pro Ala Gln Lys
1               5                   10

<210> SEQ ID NO 19
<211> LENGTH: 11
<212> TYPE: PRT
<213> ORGANISM: Homo sapiens

<400> SEQUENCE: 19

Gly Lys Asn Lys Gln Ser Leu Asp Ala Val Glu
1               5                   10

<210> SEQ ID NO 20
<211> LENGTH: 12
<212> TYPE: PRT
<213> ORGANISM: Homo sapiens

<400> SEQUENCE: 20

Ser Val Gly Met Ile Ala Gly Gly Thr Gly Ile Thr
1               5                   10

<210> SEQ ID NO 21
<211> LENGTH: 11
<212> TYPE: PRT
<213> ORGANISM: Homo sapiens

<400> SEQUENCE: 21

Ala Ile Met Lys Asp Pro Asp Asp His Thr Val
1               5                   10

<210> SEQ ID NO 22
<211> LENGTH: 12
<212> TYPE: PRT
<213> ORGANISM: Homo sapiens

<400> SEQUENCE: 22

Met Ile Gln Tyr Ala Cys Leu Pro Asn Leu Asp His
1               5                   10

<210> SEQ ID NO 23
<211> LENGTH: 10
<212> TYPE: PRT
<213> ORGANISM: Homo sapiens

<400> SEQUENCE: 23

Trp Thr Ser Phe Leu Ser Gly Val Asn Ile
1               5                   10

<210> SEQ ID NO 24
<211> LENGTH: 14
<212> TYPE: PRT
<213> ORGANISM: Homo sapiens

<400> SEQUENCE: 24

Gly Leu Lys Met Val Val Pro Gly Leu Asp Gly Ala Gln Ile
1               5                   10

<210> SEQ ID NO 25
<211> LENGTH: 14
<212> TYPE: PRT
```

<213> ORGANISM: Homo sapiens

<400> SEQUENCE: 25

Met Gln Thr Gln Gln Met Leu Leu Asn Lys Glu Glu Ala Val
1               5                   10

<210> SEQ ID NO 26
<211> LENGTH: 14
<212> TYPE: PRT
<213> ORGANISM: Homo sapiens

<400> SEQUENCE: 26

Glu Asp Gly Gly Ile Ile Arg Arg Ile Gly Thr Arg Gly Glu
1               5                   10

<210> SEQ ID NO 27
<211> LENGTH: 12
<212> TYPE: PRT
<213> ORGANISM: Homo sapiens

<400> SEQUENCE: 27

His Ile Pro Gln Ala Lys Ala Leu Leu Gln Asp Lys
1               5                   10

<210> SEQ ID NO 28
<211> LENGTH: 14
<212> TYPE: PRT
<213> ORGANISM: Homo sapiens

<400> SEQUENCE: 28

Asp Pro Leu Gly Lys Gln Gly Tyr Gln Leu Arg Gln Gly Asp
1               5                   10

<210> SEQ ID NO 29
<211> LENGTH: 12
<212> TYPE: PRT
<213> ORGANISM: Homo sapiens

<400> SEQUENCE: 29

Ile Gly Gly Pro Arg Ser Tyr Thr Ile Ala Val Ala
1               5                   10

<210> SEQ ID NO 30
<211> LENGTH: 10
<212> TYPE: PRT
<213> ORGANISM: Homo sapiens

<400> SEQUENCE: 30

His Pro Cys Arg Gln Pro Asp Thr Pro Thr
1               5                   10

<210> SEQ ID NO 31
<211> LENGTH: 15
<212> TYPE: PRT
<213> ORGANISM: Homo sapiens

<400> SEQUENCE: 31

Ala Thr Gln Cys Ile Ser Asp Gly Lys Leu Asn Glu Gly His Thr
1               5                   10                  15

<210> SEQ ID NO 32
<211> LENGTH: 13
<212> TYPE: PRT
<213> ORGANISM: Homo sapiens

<400> SEQUENCE: 32

Trp Trp Lys Ala Gln Ser Leu Thr Thr Gly Gln Glu Gly
1               5                   10

<210> SEQ ID NO 33
<211> LENGTH: 9
<212> TYPE: PRT
<213> ORGANISM: Homo sapiens

<400> SEQUENCE: 33

Arg Gln Leu Leu Ala Pro Gly Asn Thr
1               5

<210> SEQ ID NO 34
<211> LENGTH: 12
<212> TYPE: PRT
<213> ORGANISM: Homo sapiens

<400> SEQUENCE: 34

Cys Asn Pro Asp Asp Met Ala Arg Asp Leu Glu Gln
1               5                   10

<210> SEQ ID NO 35
<211> LENGTH: 17
<212> TYPE: PRT
<213> ORGANISM: Homo sapiens

<400> SEQUENCE: 35

Ser Phe Val Pro Trp Gln Pro Arg Phe Met Ile His Met Cys Pro Ser
1               5                   10                  15

Thr

<210> SEQ ID NO 36
<211> LENGTH: 12
<212> TYPE: PRT
<213> ORGANISM: Homo sapiens

<400> SEQUENCE: 36

Lys Glu Val Phe Ser Gly Ile Lys Asn Ser Asn Glu
1               5                   10

<210> SEQ ID NO 37
<211> LENGTH: 15
<212> TYPE: PRT
<213> ORGANISM: Homo sapiens

<400> SEQUENCE: 37

Arg Tyr Ser Trp Asp Cys Ser Pro Leu Ser Met Phe Arg Arg His
1               5                   10                  15

<210> SEQ ID NO 38
<211> LENGTH: 13
<212> TYPE: PRT
<213> ORGANISM: Homo sapiens

<400> SEQUENCE: 38

Asn Thr Glu Arg Thr Ile Tyr Val Arg Asp Pro Thr Ser
1               5                   10

<210> SEQ ID NO 39
<211> LENGTH: 10
<212> TYPE: PRT
<213> ORGANISM: Homo sapiens

<400> SEQUENCE: 39

Trp Pro Glu Ser Ala Ser Ser Pro Val
1               5

<210> SEQ ID NO 40
<211> LENGTH: 13
<212> TYPE: PRT
<213> ORGANISM: Homo sapiens

<400> SEQUENCE: 40

Asp Gly Gly Leu Arg His Trp Leu Arg Gln Asn Leu Pro
1               5                   10

<210> SEQ ID NO 41
<211> LENGTH: 11
<212> TYPE: PRT
<213> ORGANISM: Homo sapiens

<400> SEQUENCE: 41

Glu Pro Arg Asp Gly Ile Glu Pro Gly His Ile
1               5                   10

<210> SEQ ID NO 42
<211> LENGTH: 10
<212> TYPE: PRT
<213> ORGANISM: Homo sapiens

<400> SEQUENCE: 42

Asn Ser Ile Asn Thr Glu Glu Val Ile Asn
1               5                   10

<210> SEQ ID NO 43
<211> LENGTH: 10
<212> TYPE: PRT
<213> ORGANISM: Homo sapiens

<400> SEQUENCE: 43

Leu Ser Thr Leu Gly Ile Val Phe Gln Gly
1               5                   10

<210> SEQ ID NO 44
<211> LENGTH: 16
<212> TYPE: PRT
<213> ORGANISM: Homo sapiens

<400> SEQUENCE: 44

Pro Ile Ser Ser Cys Asp Thr Gly Thr Met Ala Asn Cys Glu Arg Thr
1               5                   10                  15

<210> SEQ ID NO 45
<211> LENGTH: 13
<212> TYPE: PRT
<213> ORGANISM: Homo sapiens

<400> SEQUENCE: 45

Ile Lys Pro Asp Gly Val Gln Arg Gly Leu Val Gly Glu
1               5                   10

<210> SEQ ID NO 46
<211> LENGTH: 17
<212> TYPE: PRT
<213> ORGANISM: Homo sapiens

<400> SEQUENCE: 46

```
Gln Lys Leu Gln Asp Ile Gln Arg Ala Met Glu Leu Leu Ser Ala Cys
1               5                   10                  15
Gln

<210> SEQ ID NO 47
<211> LENGTH: 10
<212> TYPE: PRT
<213> ORGANISM: Homo sapiens

<400> SEQUENCE: 47

Thr Thr Gly Gly Ser Gly Ser Met Tyr Ser
1               5                   10

<210> SEQ ID NO 48
<211> LENGTH: 14
<212> TYPE: PRT
<213> ORGANISM: Homo sapiens

<400> SEQUENCE: 48

Leu Thr Tyr Ser Ile Gly His Thr Pro Ala Asp Ala Arg Ile
1               5                   10

<210> SEQ ID NO 49
<211> LENGTH: 14
<212> TYPE: PRT
<213> ORGANISM: Homo sapiens

<400> SEQUENCE: 49

Leu Phe Asp Leu Asn Phe Gln Ala Gly Phe Leu Met Lys Lys
1               5                   10

<210> SEQ ID NO 50
<211> LENGTH: 12
<212> TYPE: PRT
<213> ORGANISM: Homo sapiens

<400> SEQUENCE: 50

Leu Gln Glu Arg Ala Val Leu Gly Ala Asn Asp Pro
1               5                   10

<210> SEQ ID NO 51
<211> LENGTH: 18
<212> TYPE: PRT
<213> ORGANISM: Homo sapiens

<400> SEQUENCE: 51

Thr Ala Ile Arg Pro His Gly Ile Phe Gly Pro Arg Asp Pro Gln Leu
1               5                   10                  15
Val Pro

<210> SEQ ID NO 52
<211> LENGTH: 15
<212> TYPE: PRT
<213> ORGANISM: Homo sapiens

<400> SEQUENCE: 52

Ser Gly Ser Ser Gln Gly Arg Asn Ser Pro Ala Pro Ala Val Thr
1               5                   10                  15

<210> SEQ ID NO 53
<211> LENGTH: 14
<212> TYPE: PRT
<213> ORGANISM: Homo sapiens
```

-continued

```
<400> SEQUENCE: 53

Asn Ala Ala Thr Lys Ile Pro Thr Pro Ile Val Gly Val Lys
1               5                   10

<210> SEQ ID NO 54
<211> LENGTH: 22
<212> TYPE: PRT
<213> ORGANISM: Homo sapiens

<400> SEQUENCE: 54

Ile Ser Asp Gly Pro Ser Val Ser Ala Leu Thr Asn Gly Phe Asp Thr
1               5                   10                  15

Pro Glu Glu Arg Tyr Gln
            20

<210> SEQ ID NO 55
<211> LENGTH: 13
<212> TYPE: PRT
<213> ORGANISM: Homo sapiens

<400> SEQUENCE: 55

Tyr Asp Glu Lys Arg Ser Gln Ala Asn Gly Ala Gly Ala
1               5                   10

<210> SEQ ID NO 56
<211> LENGTH: 14
<212> TYPE: PRT
<213> ORGANISM: Homo sapiens

<400> SEQUENCE: 56

Ser Leu Asp Ser Leu Pro Gln Ala Val Arg Glu Phe Leu Glu
1               5                   10

<210> SEQ ID NO 57
<211> LENGTH: 26
<212> TYPE: PRT
<213> ORGANISM: Homo sapiens

<400> SEQUENCE: 57

Gln Arg Asp Thr Val Pro Ile Pro Lys Thr Gly Leu Ser Gln Leu Gly
1               5                   10                  15

Arg Trp Met Ser Glu Glu Asp Phe Glu Lys
            20                  25

<210> SEQ ID NO 58
<211> LENGTH: 17
<212> TYPE: PRT
<213> ORGANISM: Homo sapiens

<400> SEQUENCE: 58

Phe Pro Gly Cys Met Lys Gly Arg Thr Met Tyr Val Ile Pro Phe Ser
1               5                   10                  15

Met

<210> SEQ ID NO 59
<211> LENGTH: 14
<212> TYPE: PRT
<213> ORGANISM: Homo sapiens

<400> SEQUENCE: 59

Gly Ser Asn Tyr Trp Arg Asn Arg Val Met Met Val Ala Lys
1               5                   10
```

<210> SEQ ID NO 60
<211> LENGTH: 87
<212> TYPE: PRT
<213> ORGANISM: Homo sapiens

<400> SEQUENCE: 60

Pro Thr Leu Lys Ile Phe Arg Asp Gly Glu Ala Gly Ala Tyr Asp
1               5                   10                  15

Gly Pro Arg Thr Ala Asp Gly Ile Val Ser His Leu Lys Lys Gln Ala
            20                  25                  30

Gly Pro Ala Ser Val Pro Leu Arg Thr Glu Glu Phe Lys Lys Phe
        35                  40                  45

Ile Ser Asp Lys Asp Ala Ser Ile Val Gly Phe Phe Asp Asp Ser Phe
    50                  55                  60

Ser Glu Ala His Ser Phe Leu Lys Ala Ala Ser Asn Leu Arg Asn Asp
65                  70                  75                  80

Tyr Arg Phe Ala His Thr Asn
                85

<210> SEQ ID NO 61
<211> LENGTH: 14
<212> TYPE: PRT
<213> ORGANISM: Homo sapiens

<400> SEQUENCE: 61

Thr Leu Cys Lys Pro Ala Pro Leu Thr Gly Thr Leu Glu Val
1               5                   10

<210> SEQ ID NO 62
<211> LENGTH: 11
<212> TYPE: PRT
<213> ORGANISM: Homo sapiens

<400> SEQUENCE: 62

Asp Ser Arg Pro Pro Phe Leu Ser Arg Pro Ala
1               5                   10

<210> SEQ ID NO 63
<211> LENGTH: 10
<212> TYPE: PRT
<213> ORGANISM: Homo sapiens

<400> SEQUENCE: 63

Leu Tyr Ser Arg Ser Gly Ser Leu Ser Gly
1               5                   10

<210> SEQ ID NO 64
<211> LENGTH: 21
<212> TYPE: PRT
<213> ORGANISM: Homo sapiens

<400> SEQUENCE: 64

Pro Glu Thr Arg Thr Val Ala Val Lys Gln Leu Gly Val Asn Pro Ser
1               5                   10                  15

Thr Thr Gly Thr Gln
            20

<210> SEQ ID NO 65
<211> LENGTH: 15
<212> TYPE: PRT
<213> ORGANISM: Homo sapiens

```
<400> SEQUENCE: 65

Leu Val Asn Gly Leu His Pro Leu Thr Leu Arg Trp Glu Glu Thr
1               5                   10                  15

<210> SEQ ID NO 66
<211> LENGTH: 14
<212> TYPE: PRT
<213> ORGANISM: Homo sapiens

<400> SEQUENCE: 66

Gln Pro Asp Thr Pro Pro Gly Thr Pro Leu Val Gln Asp Glu
1               5                   10

<210> SEQ ID NO 67
<211> LENGTH: 14
<212> TYPE: PRT
<213> ORGANISM: Homo sapiens

<400> SEQUENCE: 67

Leu Glu Pro Met Ala Ala Lys Ala Trp Asp Lys Glu Ser Glu
1               5                   10

<210> SEQ ID NO 68
<211> LENGTH: 15
<212> TYPE: PRT
<213> ORGANISM: Homo sapiens

<400> SEQUENCE: 68

Lys Phe Asp Trp Thr Phe Glu Gln Thr Val Glu Thr Ala Ile Thr
1               5                   10                  15

<210> SEQ ID NO 69
<211> LENGTH: 15
<212> TYPE: PRT
<213> ORGANISM: Homo sapiens

<400> SEQUENCE: 69

Gln Thr Glu Ala Arg Asp Leu Val Glu Arg Cys Met Arg Val Leu
1               5                   10                  15

<210> SEQ ID NO 70
<211> LENGTH: 21
<212> TYPE: PRT
<213> ORGANISM: Homo sapiens

<400> SEQUENCE: 70

Asp Pro His Gln Arg Leu Thr Ala Lys Gln Val Leu Gln His Pro Trp
1               5                   10                  15

Val Thr Gln Lys Asp
            20

<210> SEQ ID NO 71
<211> LENGTH: 22
<212> TYPE: PRT
<213> ORGANISM: Homo sapiens

<400> SEQUENCE: 71

Gln Leu Lys Pro Ile Glu Ser Ser Ile Leu Gln Arg Arg Val Arg Lys
1               5                   10                  15

Leu Pro Ser Thr Thr Leu
            20

<210> SEQ ID NO 72
```

```
<211> LENGTH: 16
<212> TYPE: PRT
<213> ORGANISM: Homo sapiens

<400> SEQUENCE: 72

Ser Cys Met Ala Asn Ile Asn Gly Gly Asn Thr Lys Ala Cys Thr Arg
1               5                   10                  15

<210> SEQ ID NO 73
<211> LENGTH: 14
<212> TYPE: PRT
<213> ORGANISM: Homo sapiens

<400> SEQUENCE: 73

Thr Asn Leu Asn Lys Val Ser Lys Ile Tyr Pro Leu Pro His
1               5                   10

<210> SEQ ID NO 74
<211> LENGTH: 10
<212> TYPE: PRT
<213> ORGANISM: Homo sapiens

<400> SEQUENCE: 74

Val Pro Asp Leu Ser Asn Phe Tyr Ala Gln
1               5                   10

<210> SEQ ID NO 75
<211> LENGTH: 26
<212> TYPE: PRT
<213> ORGANISM: Homo sapiens

<400> SEQUENCE: 75

Pro Val Gln Gly Ile Ile Asn Phe Glu Gln Lys Glu Ser Asn Gly Pro
1               5                   10                  15

Val Lys Val Trp Gly Ser Ile Lys Gly Leu
            20                  25

<210> SEQ ID NO 76
<211> LENGTH: 17
<212> TYPE: PRT
<213> ORGANISM: Homo sapiens

<400> SEQUENCE: 76

Glu Phe Gly Asp Asn Thr Ala Gly Cys Thr Ser Ala Gly Pro His Phe
1               5                   10                  15

Asn

<210> SEQ ID NO 77
<211> LENGTH: 14
<212> TYPE: PRT
<213> ORGANISM: Homo sapiens

<400> SEQUENCE: 77

Ile Gly Leu Asp Thr Thr Ile Met Met Arg Ser Ile Pro Leu
1               5                   10

<210> SEQ ID NO 78
<211> LENGTH: 10
<212> TYPE: PRT
<213> ORGANISM: Homo sapiens

<400> SEQUENCE: 78

Gly Phe Asp Gln Gln Met Ser Ser Met Val
1               5                   10
```

<210> SEQ ID NO 79
<211> LENGTH: 10
<212> TYPE: PRT
<213> ORGANISM: Homo sapiens

<400> SEQUENCE: 79

Asp Ser Thr Thr Lys Glu Asp Thr Gly Thr
1               5                   10

<210> SEQ ID NO 80
<211> LENGTH: 10
<212> TYPE: PRT
<213> ORGANISM: Homo sapiens

<400> SEQUENCE: 80

Lys Gln Thr Ile Gly Asn Ser Cys Gly Thr
1               5                   10

<210> SEQ ID NO 81
<211> LENGTH: 16
<212> TYPE: PRT
<213> ORGANISM: Homo sapiens

<400> SEQUENCE: 81

Asp Gly His Leu Tyr Glu Leu Asp Gly Arg Met Pro Phe Pro Val Asn
1               5                   10                  15

<210> SEQ ID NO 82
<211> LENGTH: 11
<212> TYPE: PRT
<213> ORGANISM: Homo sapiens

<400> SEQUENCE: 82

Thr Gln Ser Lys Glu Ala Phe Ala Ile Gly Leu
1               5                   10

<210> SEQ ID NO 83
<211> LENGTH: 10
<212> TYPE: PRT
<213> ORGANISM: Homo sapiens

<400> SEQUENCE: 83

Val Ala Arg Met Ile Ile Glu Ala Leu Asp
1               5                   10

<210> SEQ ID NO 84
<211> LENGTH: 12
<212> TYPE: PRT
<213> ORGANISM: Homo sapiens

<400> SEQUENCE: 84

Ser Met Asp Ser Phe Tyr Lys Val Leu Thr Glu Gln
1               5                   10

<210> SEQ ID NO 85
<211> LENGTH: 18
<212> TYPE: PRT
<213> ORGANISM: Homo sapiens

<400> SEQUENCE: 85

Ser Ala Lys Arg His Leu Ala Glu Gln Phe Ala Val Gly Glu Ile Ile
1               5                   10                  15

Thr Asp

```
<210> SEQ ID NO 86
<211> LENGTH: 14
<212> TYPE: PRT
<213> ORGANISM: Homo sapiens

<400> SEQUENCE: 86

Lys Val Glu Ser Asp Asn Gly Pro Leu Phe Thr Glu Leu Lys
1               5                   10

<210> SEQ ID NO 87
<211> LENGTH: 19
<212> TYPE: PRT
<213> ORGANISM: Homo sapiens

<400> SEQUENCE: 87

Asn Gly Lys Ser Tyr Arg Phe Met Ile Met Asp Arg Phe Gly Ser Asp
1               5                   10                  15

Leu Gln Lys

<210> SEQ ID NO 88
<211> LENGTH: 15
<212> TYPE: PRT
<213> ORGANISM: Homo sapiens

<400> SEQUENCE: 88

Ser Glu Thr Phe Glu Lys Ser Arg Leu Tyr Gln Leu Asp Lys Ser
1               5                   10                  15
```

METHODS FOR SYNTHESIS OF AN OLIGOPEPTIDE MICROARRAY

CROSS-REFERENCE TO RELATED APPLICATIONS

The present application claims the benefit of U.S. Provisional Application 61/454,156, filed Mar. 18, 2011, which is incorporated herein by reference in its entirety.

FIELD OF THE INVENTION

The present invention relates to an oligopeptide microarray and methods for the synthesis thereof. The present invention further relates to an oligopeptide microarray comprising at least about 10,000 oligopeptide features per $cm^2$ or at least about 50,000 oligopeptide features per $cm^2$.

BACKGROUND OF THE INVENTION

Oligopeptide microarrays are widely used in research and healthcare. Within these areas, oligopeptide microarrays are suitable for many different applications. Oligopeptide microarrays for example provide a tool for the identification of biologically active motifs, e.g., oligopeptide microarrays may imitate potential active motifs of ligands for screening the binding to corresponding receptors. Furthermore, the oligopeptide microarrays might reflect specific sequences of disease associated antigens. Such oligopeptide microarrays can be utilized to detect antibodies from patient samples suggesting the presence of certain inflammatory diseases and infections. Another important application of the oligopeptide microarrays is the discovery of biochemical interactions, including the binding of proteins or DNA. Oligopeptide microarrays can further be used for profiling cellular activity, enzymatic activity, cell adhesion, and the like.

Different methods for the production of oligopeptide microarrays are known in the state of the art. Spotting prefabricated peptides or in-situ synthesis by spotting reagents, e.g., on membranes, prevail. One of the most commonly used methods to generate peptide arrays of higher density are the so-called photolithographic techniques, where the synthetic design of the desired biopolymers is controlled by suitable photolabile protecting groups (PLPG) releasing the linkage site for the respective next component (amino acid, oligonucleotide) upon exposure to electromagnetic radiation, preferably light (Fodor et al., (1993) *Nature* 364:555-556; Fodor et al., (1991) *Science* 251:767-773).

Two different photolithographic techniques are known in the state of the art: 1) A photolithographic mask is used to direct light to specific areas of the synthesis surface effecting localized deprotection of the PLPG. The drawback of this technique is that a large number of masking steps are required resulting in a relatively low overall yield and high costs, e.g., the synthesis of a peptide of only six amino acids in length could require over 100 masks. 2) The second technique is the so-called maskless photolithography, where light is directed to specific areas of the synthesis surface effecting localized deprotection of the PLPG by digital projection technologies, such as micromirror devices (Singh-Gasson et al., *Nature Biotechn.* 17 (1999) 974-978). Thus, time-consuming and expensive production of exposure masks is eliminated.

The use of PLPG, providing the basis for the photolithography based synthesis of oligopeptide microarrays, is well known in the art. Commonly used PLPG for photolithography based biopolymer synthesis are for example α-methyl-6-nitropiperonyl-oxycarbonyl (MeNPOC) (Pease et al., *Proc. Natl. Acad. Sci. USA* (1994) 91:5022-5026), 2-(2-nitrophenyl)-propoxycarbonyl (NPPOC) (Hasan et al. (1997) *Tetrahedron* 53: 4247-4264), nitroveratryloxycarbonyl (NVOC) (Fodor et al. (1991) *Science* 251:767-773) and 2-nitrobenzyloxycarbonyl (NBOC) (Patchornik et al. (1970) 21:6333-6335).

Amino acids have been introduced in photolithographic solid-phase peptide synthesis of oligopeptide microarrays, which were protected with NPPOC as a photolabile amino protecting group, wherein glass slides were used as a support (U.S. Patent Publication No. 2005/0101763 A1). The method using NPPOC protected amino acids has the disadvantage that the half-life upon irradiation with light of all (except one) protected amino acids is within the range of approximately 2 to 3 minutes under certain conditions. In contrast, under the same conditions, NPPOC-protected tyrosine exhibits a half-life of almost 10 minutes. As the velocity of the whole synthesis process depends on the slowest sub-process, this phenomenon increases the time of the synthesis process by a factor of 3 to 4. Concomitantly, the degree of damage by photogenerated radical ions to the growing oligomers increases with increasing and excessive light dose requirement.

The object of the present invention is, therefore, the provision of a high density oligopeptide microarray with high sensitivity and a method for its synthesis not showing the above-described drawbacks. Thus, the object of the present invention is the provision of a sensitive oligopeptide microarray of high quality, which can be synthesized within a significantly shorter time period as compared to the state of the art, consequently reducing costs of production of oligopeptide microarrays.

SUMMARY OF THE INVENTION

The present invention is directed to a microarray and a method for the synthesis thereof.

One aspect of the present invention is a method for synthesizing an oligopeptide microarray, wherein the method comprises the steps of:

a) coupling to a reactive amino group attached directly or indirectly to a surface of a plastic solid support an amino acid comprising an amino group protected by a photolabile moiety selected from 2-(2-nitrophenyl)-propoxycarbonyl (NPPOC) and a derivative thereof with the proviso that the photolabile moiety is a benzoyl NPPOC derivative when the amino acid is tyrosine;

b) optionally capping unreacted amino acids;

c) optionally washing the plastic solid support;

d) photoirradiating the protected amino group such that the photoirradiated amino group is reactive; and e) repeating steps b) to d) for a predetermined number of times, whereby an oligopeptide is synthesized.

In one embodiment, photoirradiating is performed at 350 to 410 nm. In another embodiment, photoirradiating is spatially resolved. The surface of the plastic solid support can comprise ε-amino-hexanoic-acid carrying the reactive amino groups. In some cases, the plastic solid support comprises a surface and a body, where the body comprises polyolefin. In some cases, the surface of the plastic solid support has at least 50% light transmission at 350 to 410 nm. In some cases, photoirradiating is performed at 350 to 375 nm. In some cases, photoirradiating is performed at 360 to 370 nm, at 363 to 367 nm, or at 365 nm. Synthesis is performed using maskless photolithography using, for example, a digital micro mirror device.

In yet another embodiment, the amino acid residues are protected with different NPPOCs and/or NPPOC derivatives. In some cases, the NPPOC derivatives are Benzoyl-NPPOCs. In some cases, the Benzoyl-NPPOC is Benzoyl-NPPOC-Tyrosine. In some cases, substantially all of the oligopeptides are 6 to 24 amino acids in length and, in other cases, substantially all of the oligopeptides are 9 to 18 amino acids in length.

In another embodiment, photoirradiation is performed in the presence of a polar organic solvent selected from a group consisting of dimethylsulfoxide, N-methyl-2-pyrrolidone, dimethylformamide, acetonitrile, methanol, ethanol and propanol. Photoirradiation is performed in the presence of a base selected from hydrazine, hydroxylamine and imidazole. In some cases, photoirradiation is performed in the presence of a weak reducing or weak nucleophilic base.

In another embodiment, coupling occurs in less than 15 minutes, less than 10, and less than 5 minutes. Positioning of photoirradiation beams onto the solid support is controlled and adjusted over time, preferably before at least every 4th photoirradiating step (e.g., before at least every 3rd photoirradiating step, before at least every 2nd photoirradiating step, before every photoirradiating step). Methods of synthesizing an oligopeptide microarray can further comprise adjusting the position of the solid support. Adjusting can comprise adjusting the position of the micromirror device or adjusting the positions of both the micromirror device and the solid support.

In another embodiment, the microarray on the solid support comprises at least about 10,000 oligopeptide features per $cm^2$ and, in some cases, at least about 50,000 oligopeptide features per $cm^2$.

In another aspect, the present invention provides an oligopeptide microarray synthesized according to the methods provided herein. In one embodiment, a microarray provided herein comprises at least about 10,000 oligopeptide features per $cm^2$ and, in some cases, at least about 50,000 oligopeptide features per $cm^2$. In another embodiment, a microarray provided herein comprises C-terminal amino acid residues of the oligopeptides bound to a surface of the solid support via peptide bonds. In some cases, the C-terminal amino acid residues of the oligopeptides are coupled to the surface of the solid support by ε-amino-hexanoic-acid.

BRIEF DESCRIPTION OF THE DRAWINGS

FIG. 6 presents sequence information: epitopes of 52 antibodies selected from the Human Protein Atlas database on a peptide array.

FIG. 7 presents sensitivity titration of anti-PAPOLA on a peptide array.

DETAILED DESCRIPTION OF THE INVENTION

Figure 1:
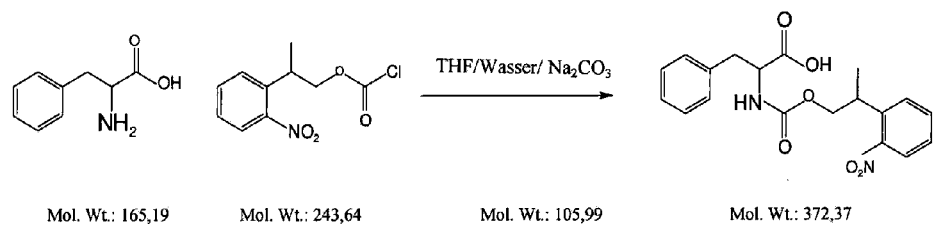
FIG. 1 illustrates synthesis of the following NPPOC-protected amino acids:
a) NPPOC-L-Phenylalanine
b) NPPOC-L-Leucine
c) NPPOC-L-Valine
Figure 1:
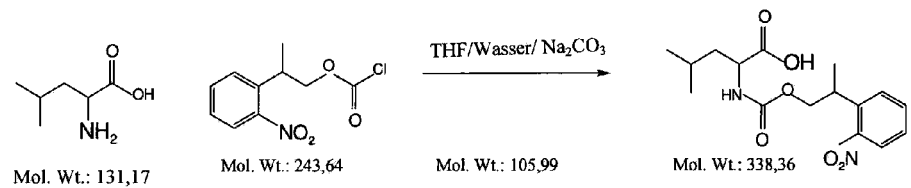
Figure 1:
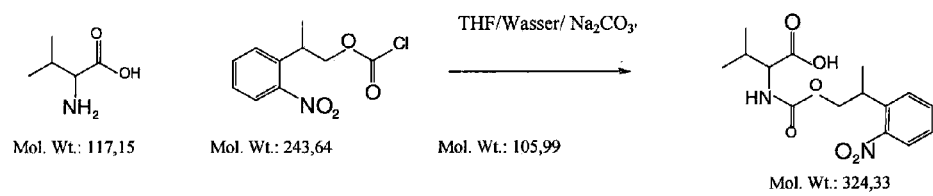

The following definitions are set forth to illustrate and define the meaning and scope of various terms used to describe the invention herein.

The term "solid or semi-solid support" as used herein refers to any solid material, having a surface area to which organic molecules can be attached through bond formation or absorbed through electronic or static interactions such as covalent bond or complex formation through a specific functional group. The support can be a combination of materials such as plastic on glass, carbon on glass, and the like. The functional surface can be simple organic molecules but can also comprise of co-polymers, dendrimers, molecular brushes and the like.

The term "plastic" as used herein refers to synthetic materials, such as homo- or hetero-co-polymers of organic building blocks (monomer) with a functionalized surface such that organic molecules can be attached through covalent bond formation or absorbed through electronic or static interactions such as through bond formation through a functional group. Preferably the term "plastic" refers to polyolefin, which is a polymer derived by polymerization of an olefin (e.g., ethylene propylene diene monomer polymer, polyisobutylene). Most preferably, the plastic is a polyolefin with defined optical properties, like TOPAS® or ZEONOR/EX®.

The term "light transmission" as used herein refers to the property of matter, whereby the matter is transparent to a certain extent such that light can pass through the matter. The amount of light passing through is dependent on the extent of transparency or transmittance.

The term "spatially resolved photoirradiation" as used herein refers to the fact that light is directed precisely onto defined areas of a surface (features), preferably the surface of a microarray, by a device, such as an array of individually addressable aluminum micro mirrors. The device controls the overall pattern of light projected on the surface, thereby preparing the areas for the next coupling reaction. Preferably, light exposure leads to the cleavage of photolabile protecting groups and the unmasking of functional groups within the areas where the next component, e.g., an amino acid or a nucleotide, is to be coupled. This system for controlled light exposure can be combined with a synthesizer to produce microarrays. This method of directing light to individually addressable aluminum micro mirrors permits synthesis of 385,000 to 4.2 million unique probe features on a single microarray of microscope-slide size of 75×25 mm.

The term "maskless photolithography" as used herein refers to a technique for the synthesis of DNA or oligopeptide microarrays without the use of photo-masks. In maskless photolithography a device is used for directing light onto a defined area of a surface, preferably the surface of a microarray, in order to induce photo reactions, preferably the release of photolabile protecting groups. Examples for such a device can be a micromirror device, a light-transmissive LCD display or a beam splitter. In some cases, the device is an array of individually addressable aluminum mirror elements that are operable under software control. Such mirror elements individually direct light onto a defined area of a surface such as the surface of a microarray. An exemplary micromirror device is the Digital Light Processor (DLP) from Texas Instruments, Inc.

The terms "microarray" or "oligopeptide microarray" as used herein refer to a two dimensional arrangement of features on the surface of a solid or semi-solid support. A single microarray or, in some cases, multiple microarrays (e.g., 3, 4, 5, or more microarrays) can be located on one solid support. The size of the microarrays depends on the number of microarrays on one solid support. The higher the number of microarrays per solid support, the smaller the arrays have to be to fit on the solid support. The arrays can be designed in any shape, but preferably they are designed as squares or rectangle. The ready to use product is the oligopeptide microarray on the solid or semi-solid support (microarray slide).

The term "feature" as used herein refers to a defined area on the surface of a microarray. The feature comprises biomolecules, such as peptides, nucleic acids, carbohydrates, and the like. One feature can contain biomolecules with different properties, such as different sequences or orientations, as compared to other features. The size of a feature is determined by two factors: i) the number of features on an array, the higher the number of features on an array, the smaller is each single feature, ii) the number of individually addressable aluminum mirror elements which are used for the irradiation of one feature. The higher the number of mirror elements used for the irradiation of one feature, the bigger is each single feature. The number of features on an array is limited by the number of mirror elements (pixels) present in the micro mirror device. The micro mirror device from Texas Instruments, Inc. currently contains 4.2 million mirror elements (pixels). The number of features within one single microarray is therefore currently limited by this number.

The term "density" as used herein refers to the number of features relative to the entire area of the solid or semi-solid support. Exemplarily, the entire area of a solid or semi-solid support with a size of 75×25 mm is 18.75 cm$^2$. The microarray according to the invention can have a density of at least about 10,000 oligopeptide features and preferably at least about 50,000 oligopeptide features per cm$^2$ relative to the entire area of 18.75 cm$^2$ of the solid or semi-solid support. In this regard, the density corresponding to the area of a microarray itself is higher. Exemplarily, the density of at least about 10,000 oligopeptide features and preferably at least 50,000 oligopeptide features relative to the entire area of 18.75 cm$^2$ of the microarray conveyed to an exemplary size of 19×14 mm (2.66 cm$^2$) of the microarray itself results in a density of at least about 70,000 oligopeptide features and preferably at least about 350,000 oligopeptide features per cm$^2$. Theoretically the density is limited by two factors: (1) the number of mirror elements (pixels) and (2) the wavelength of the light used for deprotection.

The term "protecting group" as used herein refers to a substituent, functional group, ligand, or the like, which is cleavably bound (e.g., via covalent bond, ionic bond, or complex) to a potentially reactive functional group and prevents the potentially reactive functional group from reacting in an uncontrolled manner. Preferably, the protecting group is cleavably bound via a covalent bond. The protecting group can be cleaved off the respective reactive functional group by any fashion, such as by acids, bases, fluoride, enzymes, reduction or oxidation. Preferably, the protecting group is cleaved off by light exposure. Protecting groups according to the invention are photo labile protecting groups, which include, but are not limited to, o-nitrobenzyl-oxycarbonyl (NBOC), o-nitrophenyl-ethoxycarbonyl (NPEOC), 2-(3,4-methylenedioxy-2-nitrophenyl)-propyloxy-carbonyl (MeNPPOC), 2-(3,4-methylenedioxy-2-nitrophenyl)-oxycarbonyl (MeNPOC), 2-(2-nitrophenyl)-propoxycarbonyl (NPPOC), 2-(2-nitro-4-benzoylphenyl)-2'-propyl-1'-oxycarbonyl (Benzoyl-NPPOC), dimethoxy-benzo-inylyl-oxycarbonyl (DMBOC), 2-(2-nitrophenyl)-ethylsulfonyl (NPES), (2-nitrophenyl)-propylsulfonyl (NPPS), and the like.

The term "functional group" as used herein refers to any of numerous combinations of atoms that form parts of chemical molecules, that undergo characteristic reactions themselves, and that influence the reactivity of the remainder of the molecule. Typical functional groups include, but are not limited to, hydroxyl, carboxyl, aldehyde, carbonyl, amino, azide, alkynyl, thiol and nitril. Potentially reactive functional groups include, for example, amines, carboxylic acids, alcohols, double bonds, and the like. Preferred functional groups are potentially reactive functional groups of amino acids such as amino groups or carboxyl groups.

The term "scavenger molecule" as used herein refers to an agent reactive with free radicals. In some cases, a scavenger molecule reacts with olefins by means of an addition reaction. A scavenger molecule can be contained in polar organic solvents in order to react with side products of the deprotection step. Scavenger molecules include but are not limited to strong nucleophilic amines like piperidine, piperazine, imidazole and the like as well as radical quenchers, such as hydroxylamine, TEMPO, Oxo-TEMPO, sterically hindered phenols and thiophenols.

The term "natural amino acid" as used herein refers to one of the 20 amino acids used for protein biosynthesis as well as other amino acids which can be incorporated into proteins during translation (including pyrrolysine and selenocysteine). The 20 natural amino acids include histidine, alanine, valine, glycine, leucine, isoleucine, aspartic acid, glutamic acid, serine, glutamine, asparagine, threonine, arginine, proline, phenylalanine, tyrosine, tryptophan, cysteine, methionine and lysine.

The term "non-natural amino acid" as used herein refers to an organic compound that is not among those encoded by the standard genetic code, or incorporated into proteins during translation. Therefore, non-natural amino acids include amino acids or analogs of amino acids, but are not limited to, the D-isostereomers of amino acids, the beta-amino-analogs of amino acids, citrulline, homocitrulline, homoarginine, hydroxyproline, homoproline, ornithine, 4-amino-phenylalanine, cyclohexylalanine, α-aminoisobutyric acid, N-methyl-alanine, N-methyl-glycine, norleucine, N-methyl-glutamic acid, tert-butylglycine, α-aminobutyric acid, tert-butylalanine, 2-aminoisobutyric acid, α-aminoisobutyric acid, 2-aminoindane-2-carboxylic acid, selenomethionine, dehydroalanine, lanthionine, γ-amino butyric acid, and derivatives thereof wherein the amine nitrogen has been mono- or di-alkylated.

The terms "peptide" or "oligopeptide" as used herein refer to organic compounds composed of amino acids, which are arranged in a linear chain and joined together by peptide bonds between the carboxyl and amino groups of adjacent amino acid residues. The terms "peptide" or "oligopeptide" also refer to organic compounds composed of less than 70 amino acid residues, less than 35 amino acid residues, and less than 25 amino acid residues.

The term "amino group" as used herein refers to primary (—NH$_2$), or secondary (—NHRi) amino groups. Examples of amino groups include, but are not limited to, —NH$_2$, —NHCH$_3$, —NHC(CH$_3$)$_2$. Examples of cyclic amino groups include, but are not limited to, aziridino, azetidino, pyrrolidino, piperidino, piperazino, morpholino, and thiomorpholino.

The term "reactive amino group" as used herein refers to an amine that can react with a functional group to form a covalent bond between the nitrogen of the amino group and the electrophile of the functional group, such as a peptide bond.

The term "polar organic solvent" as used herein refers to solvents which are water soluble in that a homogeneous mixture of the solvent in water is possible at room temperature under ambient conditions. Preferred polar organic solvents are methanol, ethanol, propanol, methyl ethyl ketone, acetonitrile, acetone, tetrahydrofuran (THF), dioxane, dimethylsulfoxide (DMSO), n-methyl-2-pyrrolidone (NMP), dimethylformamide (DMF), dimethylacetamide (DMA).

The term "base" as used herein refers to a substance capable of accepting a proton in polar or non-polar solvents. The base of choice for a particular reaction depends on the starting materials, the solvent and the temperature used for a specific reaction. Examples of bases include carbonate salts, phosphates, halides, hydroxides, hydrides, heterocyclic amines, disilylamides, trialkylamines, bicyclic amines, alkali metal hydrides, nitrogen-containing bases.

The term "synthesis cycle" as used herein refers to a predetermined number of successive reaction steps which are conducted to perform a synthesis of oligopeptides. More particularly, the term "synthesis cycle" refers to a predetermined number of successive reaction steps which are conducted using solid phase synthesis of oligopeptides in order to attach the respective next amino acid to the previous functional group. An oligopeptide synthesis comprises a predetermined number of synthesis cycles, wherein in each cycle one specific amino acid is attached to the previous functional group. Therefore, the number of the cycles depends on the number of amino acids of the oligopeptide. For example, for the synthesis of a peptide micro array containing 20 amino acid building blocks, 20 cycles are required to elongate each feature of the peptide microarray by one amino acid residue. The combination of amino acid residues within an oligopeptide depends on the specific amino acids, which are attached one after another to the respective previous functional group during the successive synthesis cycles.

One aspect of the present invention is a method for synthesizing an oligopeptide microarray, wherein the method comprises the steps of:
a) coupling to a reactive amino group attached directly or indirectly to a surface of a plastic solid support an amino acid comprising an amino group protected by a photolabile moiety selected from 2-(2-nitrophenyl)-propoxycarbonyl (NPPOC) and a derivative thereof with the proviso that the photolabile moiety is a benzoyl NPPOC derivative when the amino acid is tyrosine;
b) optionally capping unreacted amino acids;
c) optionally washing the plastic solid support;
d) photoirradiating the protected amino group such that the photoirradiated amino group is reactive; and
e) repeating steps b) to d) for a predetermined number of times, whereby an oligopeptide is synthesized.

In another embodiment, a method for synthesizing an oligopeptide microarray comprises the steps of:
a) coupling to a reactive amino group attached directly or indirectly to a surface of a solid support an amino acid comprising an amino group protected by a photolabile moiety selected from 2-(2-nitrophenyl)-propoxycarbonyl (NPPOC) and a derivative thereof with the proviso that the photolabile moiety is a benzoyl NPPOC derivative when the amino acid is tyrosine;
b) optionally capping unreacted amino acids;
c) optionally washing the solid support;
d) site selectively photoirradiating the protected amino group at 350 to 410 nm using a mask or a maskless device, preferably in a polar organic solvent, most preferably containing a scavenger molecule which reacts with side products of the photoirradiating step; and
e) repeating steps b) to d) for a predetermined number of times.

In another embodiment, a method for synthesizing an oligopeptide microarray comprises the steps of:
a) coupling to a reactive amino group attached directly or indirectly to a surface of a solid support an amino acid comprising an amino group protected by a photolabile moiety selected from 2-(2-nitrophenyl)-propoxycarbonyl (NPPOC) and a derivative thereof with the proviso that the photolabile moiety is a benzoyl NPPOC derivative when the amino acid is tyrosine;
b) optionally capping unreacted amino acids;
c) optionally washing the solid support;
d) site selectively photoirradiating the protected amino group at 350 to 410 nm using a mask or a maskless device, preferably in a polar organic solvent, most preferably containing a scavenger molecule which reacts with side products of the photoirradiating step;
e) repeating steps b) to d) for a predetermined number of times;
f) photoirradiating all "permanent protection groups" located at the side-chains of amino acids, e.g., Lysine(e-amino-BOC)—; and
g) optionally reversing oxidative damage occurring at Cysteine- or Methionine-sulfur by treating the oligopeptide microarray with a reducing agent.

Experimental evidence from the inventors has shown that plastic provides advantages over glass in peptide array technology. Plastic derived supports exhibit a significant reduction of non-specific binding of proteins within a sample. Non-specific binding especially of low abundance proteins may lead to the loss of important information, in case such proteins play a role in the phenomenon which is analyzed on the peptide array.

The support according to the invention is a plastic solid support. In one embodiment, the support comprises a surface and a body, wherein the body consists of polyolefin. The surface of the support can comprise reactive amino groups. In some cases, the surface comprises ε-amino-hexanoic-acid. The support can be provided in any shape, such as beads, gels, plates, membranes, slides or preferably chips. In one embodiment the C-terminal amino acid residues are bound to the surface of the support (e.g., a plastic solid support) via peptide bonds. In another embodiment, the C-terminal amino acids of the oligopeptides are coupled to the surface of the support using ε-amino-hexanoic-acid.

The surface of the support comprises functional groups capable of forming bonds such as peptide bonds. Preferably the surface of the support can be coated with a respective compound which then provides the functional groups capable of forming the bonds. In yet another embodiment, the surface comprises ε-amino-hexanoic-acid.

The first amino acid, which is coupled to the support, and the following amino acids coupled thereto are protected by any protecting group capable of preventing the potentially reactive functional group of the amino acid from reacting under certain reaction conditions. Preferred protecting groups are o-nitro-benzyloxy-carbonyl (NBOC), o-nitrophenyl-ethoxycarbonyl (NPEOC), 2-(3,4-methylenedioxy-2-nitrophenyl)-propyloxy-carbonyl (MeNPPOC), 2-(3,4-methylenedioxy-2-nitrophenyl)-oxycarbonyl (MeNPOC), dimethoxy-benzo-inylyl-oxycarbonyl (DMBOC), 2-(2-nitrophenyl)-ethylsulfonyl (NPES) and (2-nitrophenyl)-propylsulfonyl (NPPS). Exemplary protecting groups are 2-(2-nitrophenyl)-propoxycarbonyl (NPPOC), or derivatives thereof such as 2-(2-nitro-4-benzoylphenyl)-2'-propyl-1'-oxycarbonyl (Benzoyl-NPPOC). In some embodiments, the protecting groups are NPPOCs and/or NPPOC derivative. In some cases, the derivatives are 2-(2-nitro-4-benzoyl-phenyl)-propoxycarbonyl (Benzoyl-NPPOCs).

In one embodiment any natural or non-natural amino acid protected by the above-mentioned protecting groups can be used for the synthesis of peptide microarrays. Preferably, natural amino acids are used for the synthesis of oligopeptide microarrays. In a specific embodiment the amino acids are protected by NPPOCs and/or NPPOC derivatives, such as Benzoyl-NPPOC. Amino acids including Benzoyl-NPPOC-protected tyrosine which are protected with Benzoyl-NPPOC show a half-life of approximately 2 to 3 minutes. The drawback of using exclusively Benzoyl-NPPOC-protected amino acids is that the dissociated protecting groups adhere to the solid support, thereby inhibiting the synthesis process of the oligopeptides. This phenomenon is unknown for DNA arrays and has been attributed to light induced addition of the released benzophenone moiety to either the growing peptide chain or the solid support itself. In peptide array technology, plastic derived supports are preferred due to their low non-specific binding to proteins samples. However, benzophenone moieties are known to bind to hydrocarbons as present in plastic surfaces by a radical mechanism thereby inhibiting the synthesis process, which results in low quality of the synthesized oligopeptides.

16-19 different amino acids, such as histidine, alanine, valine, glycine, leucine, isoleucine, aspartic acid, glutamic acid, serine, glutamine, asparagine, threonine, arginine, proline, phenylalanine, tryptophan, cysteine, tyrosine, methionine and lysine, which are protected with NPPOCs and/or NPPOC derivatives are used. In a specific embodiment, the amino groups of some amino acids are protected with Benzoyl-NPPOC. For example, the amino group of tyrosine can be protected with Benzoyl-NPPOC.

Protecting groups are cleavably bound to potentially reactive functional groups of amino acids in order to prevent the potentially reactive functional groups from reacting in an uncontrolled manner. The protecting groups are preferably cleavably bound to the amino acids by a covalent binding. The protecting groups can be cleaved off the respective functional group by any fashion, such as by acids, bases, fluoride, enzymes, reduction or oxidation. Preferred is the use of photolabile protecting groups, which are cleaved off by light exposure or irradiation, respectively.

In one embodiment, irradiation can be used for cleaving off the photolabile protecting groups, which spans the whole spectrum of electromagnetic radiation. Preferred for cleaving off the photolabile protecting group is the range from UV- to the IR-light, ranging approximately from 200 nm to 700 nm. In some cases, deprotection is performed at 200 nm to 400 nm. In a specific embodiment, deprotection is performed at 350 to 410 nm, at 350 to 375 nm, at 360 to 370 nm, or at around 365 nm.

The support can be non-transparent or transparent for light in the range from UV- to the IR-light. In some cases, the support has at least 50% light transmission, at least 60% light transmission, and at least 75% light transmission in the range from UV- to the IR-light. In another embodiment the support has at least 50% light transmission, at least 60% light transmission, and at least 75% light transmission at a wavelengths of 350 to 410 nm. In some cases, the support has at least 50% light transmission, at least 60% light transmission, and at least 75% light transmission at wavelengths of 350 to 375 nm, 360 to 370 nm, or around 365 nm.

In one embodiment there is no washing step of the support between the capping step and the deprotection step of the method for synthesis of an oligopeptide microarray. In some cases, there are one or more washing steps between the capping step and the deprotection step of the method for synthesis of an oligopeptide microarray. Washing of the support can be performed by a polar organic solvent or a mixture of organic solvents.

In another embodiment, synthesis of the oligopeptide microarrays is performed using photolithography-based techniques. In such cases, a photolithographic mask is used to expose respective features to light in order to deprotect the functional groups, preferably the alpha-amino groups of the peptides, for coupling of the next amino acid. Preferably, maskless photolithography is used to direct light onto respective features on an oligopeptide microarray. For this purpose, maskless photolithography uses controllable devices, e.g., computer controlled devices, which have individually addressable elements to direct light onto respective features. Such controllable devices are selected from, but not limited to, light-transmissive LCD displays and beam splitters. Preferably, a digital micromirror device is used as a controllable device, which is an array of individually addressable aluminum mirror elements that are operable under software control. Such elements redirect light onto respective features on a microarray. In specific embodiments, a micromirror device is the Digital Light Processor (DLP) from Texas Instruments, Inc.

Photoirradiation can be spectrally limited to wavelengths of 350 to 410 nm, 350 to 375 nm, 360 to 370 nm, 363 to 367 nm, or 365 nm.

Spatial resolution by directing light onto respective features over individually addressable aluminum micro mirrors may lead to many densities of choice of oligopeptides per surface area. In one embodiment the microarray has a density of at least about 10,000 oligopeptide features and preferably at least about 50,000 oligopeptide features per $cm^2$ relative to the entire area of the solid support. The solid support according to the invention can have any size suitable for microarray slides, preferably the size of the solid support is 75×25 mm (18.75 $cm^2$). A single microarray may contain at least about 385,000 unique oligopeptide features, at least about 720,000 unique oligopeptide features, or at least about 2.1 million unique oligopeptide features. The micro mirror device from Texas Instruments, Inc. currently contains 4.2 million mirror elements (pixels). The number of oligopeptide features within one single microarray is therefore currently limited to 4.2 million unique oligopeptide features.

The microarrays of the present invention are high density microarrays that have extensive features in a compact area. Embodiments of the present microarrays can have a variety of feature densities. For example, the microarrays of the present invention can have a density of at least 10,000 oligopeptide features/$cm^2$, at least 50,000 oligopeptide features/$cm^2$, at least 100,000 oligopeptide features/$cm^2$, at least 200,000 oligopeptide features/$cm^2$, at least 300,000 oligopeptide features/$cm^2$, at least 400,000 oligopeptide features/$cm^2$, at least 500,000 oligopeptide features/$cm^2$, or at least 1,000,000 oligopeptide features/$cm^2$. Further, certain embodiments of microarrays have feature density within a variety of feature density ranges. For example, the density can comprise a range of about 10,000 to 1,000,000 oligopeptide features/$cm^2$, about 50,000 to 1,000,000 oligopeptide features/$cm^2$, about 100,000 to 1,000,000 oligopeptide features/cm$^2$, about 200,000 to 1,000,000 oligopeptide features/cm$^2$, about 300,000 to 1,000,000 oligopeptide features/cm$^2$, about 400,000 to 1,000,000 features/cm$^2$, about 500,000 to 1,000,000 oligopeptide features/cm$^2$, about 10,000 to 500,000 oligopeptide features/cm$^2$, about 50,0000 to 500,000 oligopeptide features/cm$^2$, about 100,000 to 500,000 oligopeptide features/cm$^2$, about 200,000 to 500,000 oligopeptide features/cm$^2$, or any range found within a lower level of 10,000 and an upper level of 1,000,000 oligopeptide features/cm$^2$.

The oligopeptides synthesized on the microarray can have any length and can contain any number of the same or of different amino acid residues. Preferably, the oligopeptides synthesized on the microarray have at least 25 or at least 35 amino acid residues. In some cases, substantially all of oligopeptides synthesized on the microarray are between 6 and 24 amino acids or between 9 and 18 amino acids in length. For example, at least 90%, at least 95%, at least 99%, or 100% of the oligopeptide features in a microarray provided herein can comprise between 6 and 24 amino acids or between 9 and 18 amino acids.

In another embodiment, photoirradiation is performed in the presence of an organic solvent, preferably a polar organic solvent. In some cases, photoirradiation is performed in the presence of a polar organic solvent or a mixture of solvents including, without limitation, dimethylsulfoxide, n-methyl-2-pyrrolidone, dimethylformamide, acetonitrile, methanol, ethanol, and propanol.

Deprotection, especially by photoirradiation, can be performed in the absence and in the presence of a base. Suitable bases include carbonate salts, ammonium salts, phosphates, thiolate salts, hydroxides, hydrides, heterocyclic amines, disilylamides, trialkylamines, bicyclic amines, organic acid salts and nitrogen-containing bases. In a specific embodiment, the base in which photoirradiation is performed is selected from either hydrazine, hydroxylamine or imidazole. Most preferred are weak basic, yet nucleophilic and weak reducing bases.

Methods used for the synthesis of oligopeptides or oligopeptide microarrays are designed in repeating cycles, comprising the basic steps of coupling, optionally capping, optionally washing and deprotecting. During each cycle, another amino acid is coupled to the oligopeptide. Therefore, the number of cycles is determined by the length of the synthesized oligopeptides. Each step has a defined duration dependent on the velocity of the associated chemical reaction. One limiting factor concerning the synthesis of oligopeptides or oligopeptide microarrays is the deprotection step together with the coupling step. Cleaving off the protecting group by light exposure depends on the one hand on physical parameters, such as pH, temperature, salt content, light intensity and wavelengths. On the other hand cleaving off the protecting group by light exposure depends on which amino acid is used in the respective cycle in conjunction with which protecting group. For example, the deprotection time of NPPOC-protected tyrosine is increased by a factor of 3 to 4 as compared to the remaining natural amino acids. Thus, NPPOC-protected tyrosine is the major time limiting factor of the synthesis of oligopeptides or oligopeptide microarrays. In contrast, the deprotection time of Benzoyl-NPPOC protected tyrosine is on the same level as the remaining natural amino acids protected with NPPOC. Thus, using Benzoyl-NPPOC protected tyrosine together with the remaining 19 natural amino acids protected with NPPOC leads to the removal of the major time limiting factor of the synthesis of oligopeptides or oligopeptide microarrays and thus to a significant increase in velocity. In one embodiment, the coupling step of each synthesis cycle occurs in less than 15 minutes, less than 10, or less than 5 minutes.

It is essential to have an active alignment of the oligopeptide microarray and the features, respectively, to the optical part between the synthesis cycles in order to ensure the light exposure solely on the respective features. Therefore, it is necessary to adjust the position of the oligopeptide microarray over a duration of over 36 hours accurately in one and the same position with a tolerance of about 1 µm. To achieve this goal, the oligopeptide array and the micro mirror array are both actively aligned by a control system. In another embodiment the positioning of photoirradiation beams onto the support is controlled and adjusted over time. In some cases, positioning of photoirradiation beams onto the support is controlled and adjusted before at least every 4th photoirradiation (deprotection step) and, in some cases, before every irradiation.

In one embodiment, the support can be made of any material known by the skilled person used for the synthesis of an oligopeptide microarray, preferably the support is made of plastic, glass, carbon on glass, metal on glass, or plastic on glass. Preferably, plastic is used as a support. Most preferred is a plastic solid support. In another embodiment, the adjustment is performed by means of adjusting the position of the plastic solid support.

Another aspect of the present invention is an oligopeptide microarray synthesized according to the method described above.

Yet another aspect of the present invention is an oligopeptide microarray, which is located on a support, preferably a plastic solid support, comprising a density of at least about 10,000 oligopeptide features and preferably at least about 50,000 oligopeptide features per cm$^2$. Applied to the area of a microarray, a single oligopeptide microarray may contain at least about 385,000 unique oligopeptide features, preferably at least about 720,000 unique oligopeptide features, more preferably at least about 2.1 million unique oligopeptide features.

In one embodiment, the C-terminal amino acid residues are covalently bound to the surface of the support, preferably a plastic solid support, via peptide bonds. In another embodiment the C-terminal amino acids of the oligopeptides are coupled to the surface of the support, preferably a plastic solid support, with an ε-amino-hexanoic-acid linker moiety.

The oligopeptide microarray according to the invention can be used for any application known by the skilled person, e.g., the oligopeptide microarray can be used as an immunoassay, where the surface of the of the array is blocked in a first step. Blocking is advisable in order to prevent non-specific binding of proteins or antibodies from the sample to the surface of the array based on simple adsorption or precipitation. Blocking can be performed with albumins, casein, milk powder or the like. In some cases, certain hydrolyzed fractions like alkali-soluble casein can be used. Subsequently the array can be incubated with a sample containing antibodies, which selectively bind the epitopes represented on the array. In one embodiment, the sample is diluted in a buffer containing the blocking reagent. The antibodies from the sample can then be detected using secondary antibodies carrying a label known by the skilled person. Such labels include but are not limited to fluorescence dyes, such as (Cy2, Cy3 or Cy5)™ and enzymes, such as HRP or alkaline phophatases. After extensive washing with dilute acid, guanidine or detergent, the array can be dried and analyzed.

The following Examples 1 to 5 are provided to aid the understanding of the present invention, the true scope of which is set forth in the appended claims. It is understood that modifications can be made in the procedures set forth without departing from the spirit of the invention.

EXAMPLES

Example 1

Synthesis of NPPOC-Protected Amino Acids

NPPOC-L-Phenylalanine 27.1 g L-Phenylalanine was added to a solution of 38.2 g $Na_2CO_3$ in 200 ml $H_2O$. To the clear solution 200 ml tetrahydrofurane (THF) was added. A solution of 40.0 g chlorocarbonate of 2-nitrophenyl-2-propan-1-ol (NPPOC-Cl) in 160 ml THF was added dropwise on ice. After stirring for 2 hours at 0° C., THF was removed in a rotary evaporator under vacuum and the residue was extracted 4 times with 200 ml each of a mixture of ethylacetate-hexanes 1:1. The aqueous residue was acidified to pH 2.5 with diluted HCl and extracted twice with approximately 400 ml ethylacetate. Combined extracts were washed with $H_2O$ and evaporated in vacuo to dryness. The residue was dissolved in dichloromethane and purified by column chromatography (approximately 120 g silica gel). The yield added up to 52.9 g (87%) of a colorless amorphous tarry oil. The purity was measured by HPLC and is 99%.

NPPOC-L-Leucine 21.5 g L-Leucine was added to a solution of 38.2 g $Na_2CO_3$ in 800 ml $H_2O$, Subsequently, 800 ml THF was added to the clear solution. A solution of 40.0 g NPPOC-Cl in 160 ml THF was added dropwise on ice. After stirring for 0.5 hours at 0° C., THF was removed in a rotary evaporator under vacuum and the residue was extracted 3 times with 200 ml each of a mixture of ethyl acetate/hexanes 1:1. The aqueous residue was acidified to pH 2.5 with diluted HCl and extracted twice with approximately 400 ml ethyl acetate. Combined extracts were washed with $H_2O$ and evaporated in vacuo to dryness. The residue was dissolved in dichloromethane and purified by short column chromatography (approximately 50 g silica gel). The yield added up to 53 g (95%) of a red-brownish amorphous clear oil. The purity was measured by HPLC and is 97.4%. The m/z was determined by LC/MS and is MH+: 339.4.

NPPOC-L-Valine 100 g L-valine was added to a solution of 199 g $Na_2CO_3$ in 5000 ml $H_2O$. 2500 ml THF was added to the clear solution. A solution of 207.9 g NPPOC-Cl in 1250 ml THF was added dropwise on ice. After stirring for 0.5 hours at 0° C., THF was removed in a rotary evaporator under vacuum and the residue was extracted 4 times with 1000 ml each of a mixture of ethyl acetate-hexanes 1:1. The aqueous residue was acidified to pH 2.5 with diluted HCl/Citric Acid 1:1 and extracted twice with approximately 1500 ml ethyl acetate. Combined extracts were washed with $H_2O$ and evaporated in vacuo to dryness. The residue was dissolved in dichloromethane and purified by short column chromatography (approximately 300 g silica gel). The yield added up to 226.8 g (82%) of a colorless amorphous tarry oil. The purity was measured by HPLC and is 98.5%. The m/z was determined by LC/MS and is MH+: 325.3.

NPPOC-L-Glycine 12.3 g glycine were added to a solution of 38.2 g $Na_2CO_3$ in 200 ml $H_2O$. 800 ml THF was added to the clear solution. A solution of 40.0 g NPPOC-Cl in 160 ml THF was added dropwise on ice. After stirring for 0.5 hours at 0° C., THF was removed in a rotary evaporator under vacuum and the residue was extracted 4 times with 200 ml each ethyl acetate-hexanes 1:1. The aqueous residue was acidified to pH 2.5 with diluted HCl and extracted twice with approximately 300 ml ethyl acetate. Combined extracts were washed with $H_2O$ and evaporated in vacuo to dryness. The residue was dissolved in dichloromethane and purified by column chromatography (approximately 80 g silica gel). The yield added up to 23.7 g (51%) of a reddish amorphous tarry oil. The purity was measured by HPLC and is 99.1%.

NPPOC-L-Glutamic Acid 24.2 g L-glutamic acid was added to a solution of 55.7 g $Na_2CO_3$ in 800 ml $H_2O$. 800 ml THF was added to the clear solution. A solution of 40.0 g NPPOC—Cl in 160 ml THF was added dropwise on ice. After stirring for 0.5 hours, THF was removed in a rotary evaporator under vacuum and the residue was extracted 4 times with 200 ml each ethyl acetate-hexanes 1:1. The aqueous residue was acidified to pH 2.5 with diluted HCl and extracted twice with approximately 400 ml ethyl acetate. Combined extracts were washed with $H_2O$ and evaporated in vacuo to dryness. The residue was dissolved in dichloromethane and purified by short column chromatography (approximately 100 g silica gel). The yield added up to 48.5 g (83%) of a pink amorphous foam. The purity was measured by HPLC and is 96.3%. The m/z was determined by LC/MS and is MH+: 3553.

NPPOC-(1-Trityl)-L-Histidine

In the first step, 140 ml piperidine was added to a solution of 100 g FMOC-trityl-L-histidine in 2000 ml THF. After stirring for 2 hours at RT, 2500 ml $H_2O$ was added and stirred for additional 0.5 hours. The precipitate was removed by filtration, THF was removed by distillation in a rotary evaporator and the solution was acidified to pH 2.5 with diluted HCl. After incubation overnight, the precipitate was collected by filtration, washed with small amounts of water, resuspended in a mixture of 20 ml acetic acid in 800 ml $H_2O$ and stirred for 0.5 hours. Filtration and air-drying yielded 64 g of a colorless powder (95%), which was used in the subsequent step.

In the second step, 64 g trityl-L-histidine was added to a solution of 37.5 g $Na_2CO_3$ in 2000 ml $H_2O$. 2000 ml THF was added to the clear solution. A solution of 39.0 g NPPOC—Cl in 160 ml THF was added dropwise on ice. After stirring for 0.5 hours at 0 deg, THF was removed in a rotary evaporator under vacuum and the residue was adjusted to pH 10.6 with NaOH, extracted 3 times with 1000 ml each ethyl acetate-Hexanes 1:1.

The aqueous residue was acidified to pH 2.5 with diluted HCl and extracted twice with app. 400 ml ethyl acetate. Combined extracts were washed with water and evaporated to dryness in vacuo.

The residue was dissolved in dichloromethane and purified by short column chromatography (approximately 120 g silica gel). The yield added up to 132 g (78%) of a colorless amorphous foam. The purity was measured by HPLC and is 97%.

Figure 2:
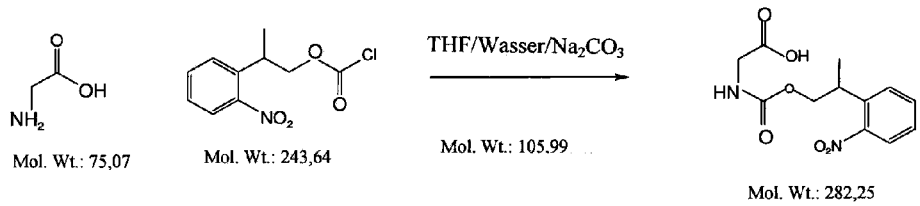
FIG. 2 illustrates synthesis of the following NPPOC-protected amino acids:
a) NPPOC-L-Glycine
b) NPPOC-L-Glutamic Acid
c) NPPOC-(1-Trityl)-L-Histidine
Figure 2:
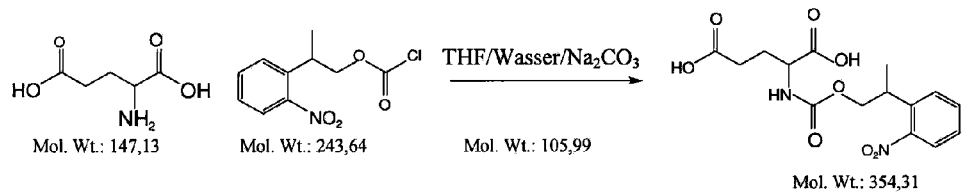
Figure 2:
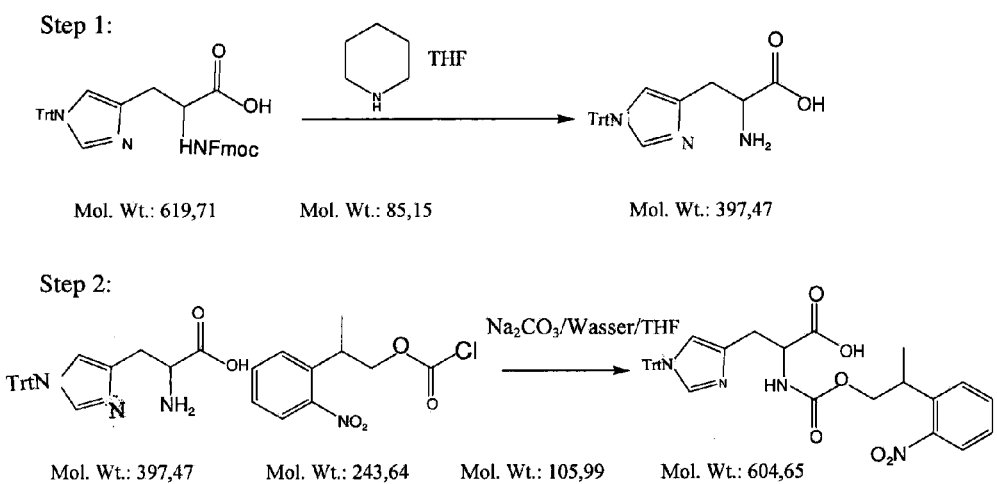
Figure 3:
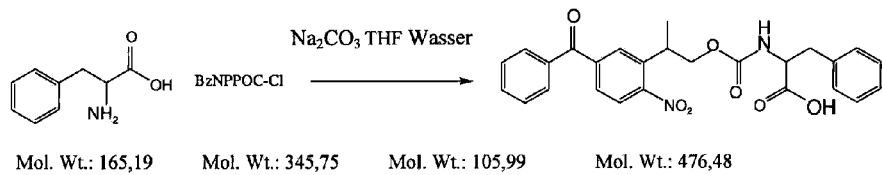
FIG. 3 illustrates synthesis of the following Benzoyl-NPPOC-protected amino acids:
a) Benzoyl-NPPOC-L-Phenylalanine
b) Benzoyl-NPPOC-L-Methionine
c) Benzoyl-NPPOC-(t-Bu)-L-Tyrosine
Figure 3:
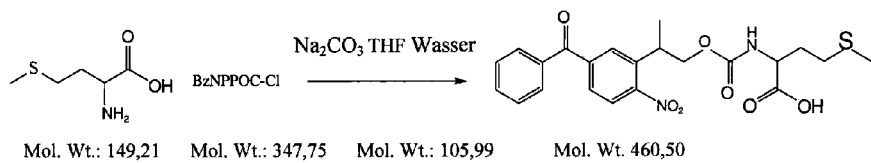
Figure 3:
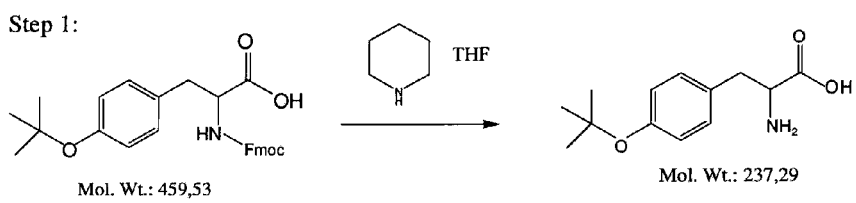
Figure 3:
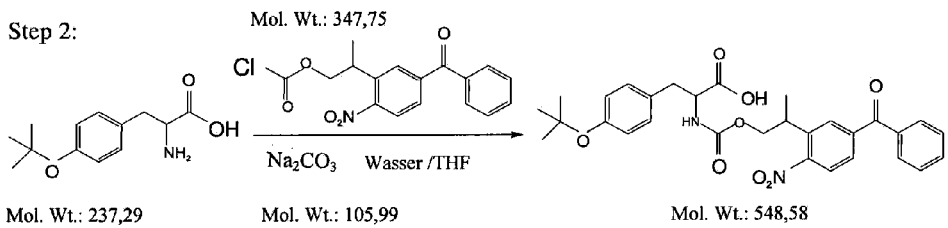

Other examples of amino acids that can be NPPOC-protected using similar 1- or 2-step processes as outlined in FIGS. 1 and 2 and described above are alanine, valine, leucine, isoleucine, aspartic acid, serine, glutamine, asparagine, threonine, arginine, proline, tryptophan, cysteine, lysine, norleucine, acetyl-lysine, hydroxyl-proline and 6-amino-hexanoic acid. Yet other examples of amino acids available from these reaction sequences would include D-amino acids, beta-amino acids and other non-natural modified amino acids.

Example 2

Synthesis of Benzoyl-NPPOC-Protected Amino Acids

Benzoyl-NPPOC-L-Phenylalanine 28.1 g L-phenylalanine was added to a solution of 39 g $Na_2CO_3$ in 830 ml $H_2O$. 830 ml THF was added to the clear solution. A solution of 59.1 g Benzoyl-NPPOC—Cl in 150 ml THF was added dropwise on ice under vigorous stirring. After addition, stirring was continued for 0.5 hours at 0° C., THF was removed in a rotary evaporator under vacuum and the residue was extracted 4 times with 200 ml each ethyl ether. The aqueous residue was acidified to pH 4 with diluted HCl and extracted twice with approximately 400 ml ethyl acetate. Combined extracts were washed with $H_2O$ and evaporated in vacuo to dryness. The residue was dissolved in dichloromethane and purified by short column chromatography (approximately 80 g silica gel). The yield added up to 55.6 g (68%) of a colorless amorphous foam. The purity was measured by HPLC and is 97%.

Benzoyl-NPPOC-L-Methionine 75.9 g L-methionine was added to a solution of 118.7 g $Na_2CO_3$ in 1700 ml $H_2O$. 1500 ml THF was added to the clear solution. A solution of 177 g benzoyl-NPPOC—Cl in 300 ml THF was added dropwise on ice. After stirring for 0.5 hours at 0° C., THF was removed in a rotary evaporator under vacuum and the residue was extracted 4 times with 200 ml each ethyl ether. The aqueous residue was acidified to pH 3 with diluted HCl and extracted twice with approximately 400 ml ethyl acetate. Combined extracts were washed with $H_2O$ and evaporated in vacuo to dryness. The residue was dissolved in dichloromethane and purified by short column chromatography with dichloromethane and dichloromethane/methanol (approximately 100 g silica gel). The yield added up to 132.8 g (57%) of a colorless amorphous foam. The purity was measured by HPLC and is 95%.

Benzoyl-NPPOC-(t-Bu)-L-Tyrosine

In the first step, 92.6 g piperidine was added to a solution of 100 g FMOC-(tBu)-L-tyrosine in 1600 ml THF. After stirring for 2 hours at RT solvents were removed by distillation in a rotary evaporator and the residue was taken up in dichloromethane and extracted twice with a solution of 23 g $Na_2CO_3$ in 600 ml $H_2O$. The combined aqueous extracts were acidified to pH 3 with diluted HCl. After incubation overnight, the precipitate was collected by filtration, washed with small amounts of $H_2O$ and subsequently air-dried. The mother liquor was concentrated to a small volume to yield another fraction of precipitate. The combined yield added up to 43.9 g of colorless needles (85%), which were used in the following step.

In the second step, 42.0 g H-Tyr(t-Bu)-OH was added to a solution of 41.3 g $Na_2CO_3$ in 500 ml $H_2O$. 500 ml THF was added to the clear solution. A solution of 61.6 g Benzoyl-NPPOC—Cl in 200 ml THF was added dropwise on ice. After stirring for 0.5 hours at RT, THF was removed in a rotary evaporator under vacuum and the residue was extracted 4 times with 200 ml each ethyl acetate/hexanes 1:1.

The aqueous residue was acidified to pH 3 with diluted HCl and extracted twice with approximately 400 ml ethyl acetate. Combined extracts were washed with water and evaporated in vacuo to dryness. The residue was dissolved in dichloromethane and purified by short column chromatography with dichloromethane and dichloromethane/methanol (approximately 100 g silica gel). The yield added up to 83 g (85%) of a colorless amorphous foam. The purity was measured by HPLC and is 95%.

Example 3

Half-Lives of NPPOC-Protected Amino Acids Upon Light-Exposure

Figures 4, 4A, 4B:
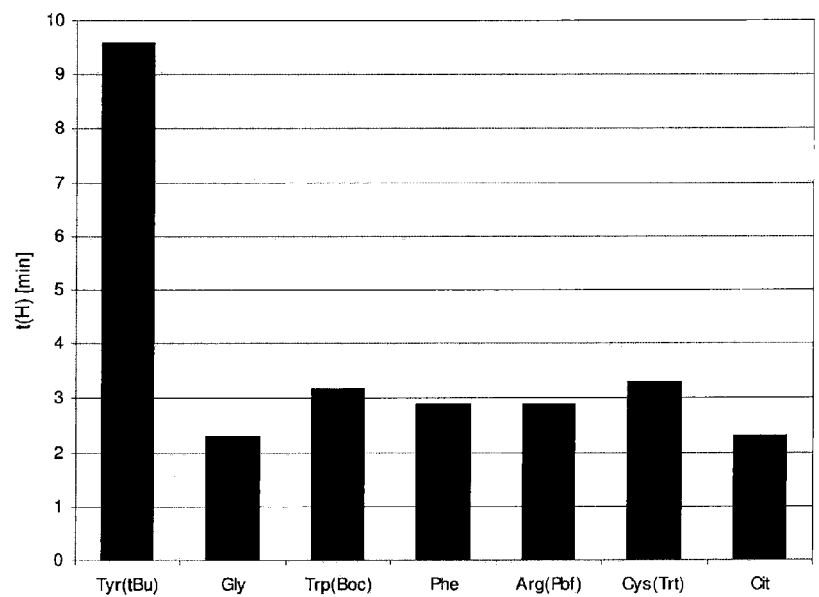
FIG. 4 presents time periods of half-lives upon exposure to light for different NPPOC-protected amino acids at a wavelength of 365 nm. Light exposure was performed for time periods where the used lamp power allows for deprotection half-lives within these time periods.

To evaluate the half-lives, NPPOC-protected amino acids were provided in a concentration of c=0.3 mmol/l solved in n-methylpyrrolidone (NMP)+0.5% hydroxylamine in UltraVettes®. Light exposure was performed at 365 nm for 2, 4, 6, 8 and 10 minutes to induce deprotection of the respective amino acids. Subsequently, the solution was analyzed by HPLC in order to evaluate the time period necessary to deprotect 50% of the initial amount of the protected amino acid. The half-lives were then extrapolated from the durations resulting from the exposure times of 2, 4, 6, 8 and 10 minutes. As can be taken from FIG. 4, in case of the half-life of NPPOC-Tyr(t-Bu)-OH a time period of 9.6 minutes was extrapolated. Thus, the time period of NPPOC-Tyr(t-Bu)-OH was increased by a factor of 3 to 4 as compared to the remaining NPPOC-protected amino acids.

Example 4

Half-Lives of Benzoyl-NPPOC-Protected Amino Acids Upon Light-Exposure

Figures 5, 5A, 5B:
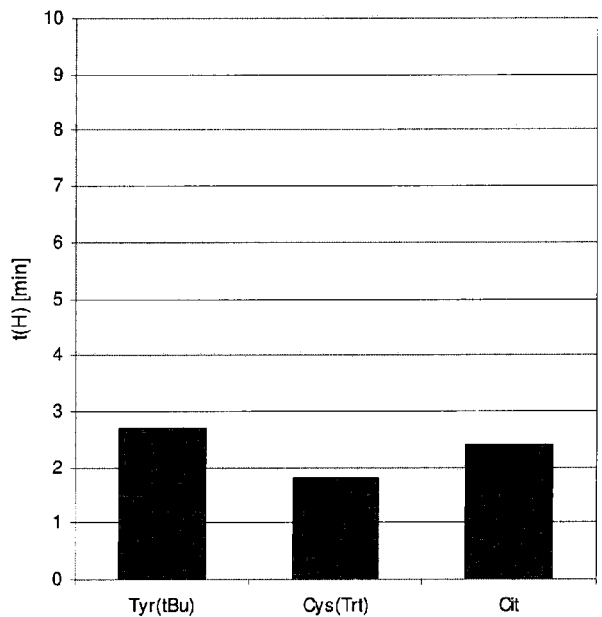
FIG. 5 presents time periods of half-lives upon exposure to light for different Benzoyl-NPPOC-protected amino acids at a wavelength of 365 nm. Light exposure was performed for time periods where the used lamp power allows for deprotection half-lives within these time periods.

To evaluate the half-lives, Benzoyl-NPPOC-protected amino acids were provided in a concentration of c=0.3 mmol/l solved in NMP+0.5% hydroxylamine in UltraVettes®. Light exposure was performed at 365 nm for 2, 4, 6, 8 and 10 minutes to induce deprotection of the respective amino acids. Subsequently, the solution was analyzed by HPLC in order to evaluate the time period necessary to deprotect 50% of the initial amount of the protected amino acid. The half-lives were then extrapolated from the durations resulting from the exposure times of 2, 4, 6, 8 and 10 minutes. As can be taken from FIG. 5, in case of the half-life of Benzoyl-NPPOC-Tyr(t-Bu)-OH a time period of 2.7 minutes was extrapolated. Thus, the time period of Benzoyl-NPPOC-Tyr(t-Bu)-OH was within the same range as compared to the remaining NPPOC-protected amino acids described in Example 3.

Example 5

Synthesis of an Oligopeptide Microarray Using the Maskless Peptide Array Synthesizer (MAS)

Oligopeptide microarrays were synthesized according to the invention. The flow cell was rinsed with NMP (peptide synthesis grade). Subsequently, 0.5 to 0.7 ml of a 60 mM solution of the NPPOC-protected α-amino acid in DMF (peptide synthesis grade) and 0.25 to 0.35 ml of 0.12 M anhydrous HBTU (O-benzotriazole-N,N,N',N'-tetramethyl-uronium-hexafluoro-phosphate) and anhydrous HOBt (N-hydroxybenzotriazole) as well as 0.25 to 0.35 ml of 0.12 M N,N-diisopropylethylamine in DMF (peptide synthesis grade) were pumped into the respective reaction chamber and mixed therein. The reaction mixture remained within the reaction chamber for the activation time of 5 minutes and was pumped subsequently into the flow cell for the coupling reaction, whereas the flow cell was overfilled by approximately 30 to 50% and another 10 to 40% of the flow cell volume remained as a buffer in the entry tubing of the flow cell. After a coupling time of 2 minutes the flow cell was initially rinsed with pure NMP (peptide synthesis grade) and subsequently the flow cell was filled with NMP containing 0.1% hydroxylamine and 0.1% $H_2O$. The filled flow cell was irradiated with light of the wavelength 365 nm for approximately 40 to 60 seconds, directly after the irradiation again rinsed with pure NMP (peptide synthesis grade) and thus prepared for the next coupling step. The software of the MAS assured during the synthesis by the appropriate selection of the bitmap for the photolithographic mask, that the solid support was exposed to light only on features, where coupling of the next amino acid was required.

Example 6

Synthesis of the Antigen Sequences of 52 Selected Antibodies

Fifty-two antibodies (see FIG. 6) were selected from the Human Protein Atlas database (proteinatlas.org on the World Wide Web). The respective antigen sequences were generated according to Example 5 in 164 successive synthesis cycles as 10-mer peptides with an overlap of 9 amino acids. Each peptide had an additional Serine residue at each end in order to improve hydrophilicity of the support bound peptide and enable easy access of antibodies. In some cases, the overlap was shorter, but none was less than 6 amino acids. Deprotected oligopeptide arrays were incubated with mixtures of antibodies at dilution factors according to the data sheet recommendation for WESTERN analysis in the manufacturer's recommended buffer and their binding epitopes were determined as the highest intensity signals upon fluorescent labeling with an anti-rabbit secondary antibody. In some cases, the arrays were washed with buffer containing 0.1% SDS in order to remove non-specific bound antibodies.

Example 7

Sensitivity Titration of Anti-PAPOLA in Buffer

A peptide array manufactured as described in Example 6 above was incubated with escalating dilutions of the anti-PAPOLA antibody (PolyA Polymerase alpha, HPA001788), from 1:10,000 up to 1:240,000 in discrete sub-arrays formed by a Roche Nimblegen 12-plex sample chamber assembly. Staining and washing was performed as described above. As depicted in FIG. 7, raw data after fluorescent scanning with a Roche Nimblegen MS 200 micro array scanner revealed the epitopes clearly visible even at the highest dilution, comparing to an antibody concentration of about 200 pg/mL, with a relative signal to noise ratio of 4:1.

What is claimed is:

1. A method for synthesizing an oligopeptide microarray, wherein the method comprises the steps of:
    a) coupling to a reactive amino group attached directly or indirectly to a surface of a plastic solid support an amino acid comprising an amino group protected by a photolabile moiety selected from 2-(2-nitrophenyl)-propoxycarbonyl (NPPOC) and a derivative thereof, with the proviso that the photolabile moiety is 2-(2-nitro-4-benzoylphenyl)-2'-propyl-1'-oxycarbonyl (benzoyl-NPPOC) when the amino acid is tyrosine wherein the method includes coupling at least one tyrosine;
    b) optionally capping unreacted amino acids;
    c) optionally washing the plastic solid support;
    d) photoirradiating the protected amino group such that the photoirradiated amino group is reactive; and
    e) repeating steps a) to d) for a predetermined number of times, whereby an oligopeptide is synthesized.

2. The method according to claim 1, wherein photoirradiating is spatially resolved.

3. The method according to claim 1, wherein the surface comprises ε-amino-hexanoic-acid.

4. The method according to claim 1, wherein the plastic solid support has at least 50% light transmission when photoirradiating is performed between 350 and 410 nm.

5. The method according to claim 1, wherein photoirradiating is performed between 350 and 410 nm.

6. The method according to claim 5, wherein photoirradiating is performed between 350 and 375 nm, between 360 and 370 nm, between 363 and 367 nm, or at 365 nm.

7. The method according to claim 1, wherein synthesizing comprises maskless photolithography.

8. The method according to claim 7, wherein maskless photolithography comprises using a digital micromirror device.

9. The method according to claim 1, wherein the amino acid is selected from the group consisting of tyrosine, histidine, alanine, valine, glycine, leucine, isoleucine, aspartic acid, glutamic acid, serine, glutamine, asparagine, threonine, arginine, proline, phenylalanine, tryptophan, cysteine, methionine, and lysine.

10. The method according to claim 1, wherein the derivative of NPPOC is benzoyl-NPPOC.

11. The method according to claim 1, wherein the predetermined number of times is between 6 and 24, whereby the oligopeptide comprises 6 to 24 amino acids.

12. The method according to claim 11, wherein the predetermined number of times is between 9 and 18, whereby the oligopeptide comprises 9 to 18 amino acids.

13. The method according to claim 1, wherein photoirradiating is performed in the presence of a polar organic solvent selected from the group consisting of dimethylsulfoxide, N-methyl-2-pyrrolidone, dimethylformamide, acetonitrile, methanol, ethanol, and propanol, or a base selected from the group consisting of hydrazine, hydroxylamine, and imidazole.

14. The method according to claim 1, wherein the step of photoirradiating occurs over a time period of less than about 5 minutes.

15. The method according to claim 1, further comprising positioning photoirradiation beams on the solid support prior to at least every 4th photoirradiating step.

16. The method according to claim 1, further comprising adjusting the position of the solid support.

17. The method according to claim 1, further comprising synthesizing a plurality of oligopeptide features on the oligopeptide microarray by performing each of the steps a) to e), wherein the oligopeptide microarray comprises at least 10,000 of the oligopeptide features per $cm^2$.

18. A method for synthesizing an oligopeptide microarray, wherein the method comprises the steps of:
   a) coupling to a reactive amino group attached directly or indirectly to a surface of a solid support an amino acid comprising an amino group protected by a photolabile moiety selected from 2-(2-nitrophenyl)-propoxycarbonyl (NPPOC) and a derivative thereof, with the proviso that the photolabile moiety is 2-(2-nitro-4-benzoylphenyl)-2'-propyl-1'-oxycarbonyl (benzoyl-NPPOC) when the amino acid is tyrosine wherein the method includes coupling at least one tyrosine;
   b) optionally capping unreacted amino acids;
   c) optionally washing the solid support;
   d) photoirradiating the protected amino group such that the photoirradiated amino group is reactive; and
   e) repeating steps a) to d) for a predetermined number of times, whereby an oligopeptide is synthesized.

19. The method according to claim 18, wherein photoirradiating is spatially resolved.

20. The method according to claim 18, wherein the surface comprises ε-amino-hexanoic-acid.

21. The method according to claim 18, wherein the solid support has at least 50% light transmission when photoirradiating is performed between 350 and 410 urn.

22. The method according to claim 18, wherein photoirradiating is performed between 350 and 410 nm.

23. The method according to claim 22, wherein photoirradiating is performed between 350 and 375 nm, between 360 and 370 nm, between 363 and 367 nm, or at 365 nm.

24. The method according to claim 18, wherein synthesizing comprises maskless photolithography.

25. The method according to claim 24, wherein maskless photolithography comprises using a digital micromirror device.

26. The method according to claim 18, wherein the amino acid is selected from the group consisting of tyrosine, histidine, alanine, valine, glycine, leucine, isoleucine, aspartic acid, glutamic acid, serine, glutamine, asparagine, threonine, arginine, proline, phenylalanine, tryptophan, cysteine, methionine, and lysine.

27. The method according to claim 18, wherein the derivative of NPPOC is benzoyl-NPPOC.

28. The method according to claim 18, wherein the predetermined number of times is between 6 and 24, whereby the oligopeptide comprises 6 to 24 amino acids.

29. The method according to claim 28, wherein the predetermined number of times is between 9 and 18, whereby the oligopeptide comprises 9 to 18 amino acids.

30. The method according to claim 18, wherein photoirradiating is performed in the presence of a polar organic solvent selected from the group consisting of dimethylsulfoxide, N-methyl-2-pyrrolidone, dimethylformamide, acetonitrile, methanol, ethanol, and propanol, or a base selected from the group consisting of hydrazine, hydroxylamine, and imidazole.

31. The method according to claim 18, wherein the step of photoirradiating occurs over a time period of less than about 5 minutes.

32. The method according to claim 18, further comprising positioning photoirradiation beams on the solid support prior to at least every 4th photoirradiating step.

33. The method according to claim 18, further comprising adjusting the position of the solid support.

34. The method according to claim 18, further comprising synthesizing a plurality of oligopeptide features on the oligopeptide microarray by performing each of the steps a) to e), wherein the oligopeptide microarray comprises at least 10,000 oligopeptide features per $cm^2$.

35. A method for synthesizing an oligopeptide microarray, wherein the method comprises the steps of:
   a) coupling to a reactive amino group attached directly or indirectly to a surface of a solid support an amino acid comprising an amino group protected by a photolabile moiety, the photolabile moiety selected from 2-(2-nitrophenyl)-propoxycarbonyl (NPPOC) and a derivative thereof;
   b) optionally capping unreacted amino acids;
   c) optionally washing the solid support;
   d) photoirradiating the protected amino group such that the photoirradiated amino group is reactive; and
   e) repeating steps a) to d) for a predetermined number of times, whereby an oligopeptide is synthesized,
   wherein the predetermined number of times is at least one,
   wherein the method includes coupling at least one tyrosine, and at least one amino acid selected from the group consisting of histidine, alanine, valine, glycine, leucine, isoleucine, aspartic acid, glutamic acid, serine, glutamine, asparagine, threonine, arginine, proline, phenylalanine, tryptophan, cysteine, methionine, and lysine,
   wherein the photolabile moiety is benzoyl-NPPOC when the amino acid is tyrosine, and
   wherein the photolabile moiety is not benzoyl-NPPOC when the amino acid is selected from the group consisting of histidine, alanine, valine, glycine, leucine, isoleucine, aspartic acid, glutamic acid, serine, glutamine, asparagine, threonine, arginine, proline, phenylalanine, tryptophan, cysteine, methionine, and lysine.

36. The method according to claim 35, wherein the step of photoirradiating occurs over a time period of less than about 5 minutes.

* * * * *